US012690773B2

(12) United States Patent
Jin et al.

(10) Patent No.: US 12,690,773 B2
(45) Date of Patent: Jul. 28, 2026

(54) BLOOD PRESSURE MEASUREMENT DEVICE

(71) Applicant: HUAWEI TECHNOLOGIES CO., LTD., Shenzhen (CN)

(72) Inventors: Junye Jin, Dongguan (CN); Bo Yang, Shenzhen (CN); Menglong Zhao, Xi'an (CN); Shiqiang Lu, Xi'an (CN); Dong Li, Dongguan (CN); Zhi Guo, Xi'an (CN); Nan Lu, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 215 days.

(21) Appl. No.: 18/715,095

(22) PCT Filed: Nov. 24, 2022

(86) PCT No.: PCT/CN2022/134174
§ 371 (c)(1),
(2) Date: May 30, 2024

(87) PCT Pub. No.: WO2023/103805
PCT Pub. Date: Jun. 15, 2023

(65) Prior Publication Data
US 2025/0025057 A1 Jan. 23, 2025

(30) Foreign Application Priority Data
Dec. 6, 2021 (CN) .......................... 202111477107.1

(51) Int. Cl.
| | |
|---|---|
| *A61B 5/00* | (2006.01) |
| *A61B 5/021* | (2006.01) |
| *A61B 5/022* | (2006.01) |

(52) U.S. Cl.
CPC ...... *A61B 5/02108* (2013.01); *A61B 5/02141* (2013.01); *A61B 5/02225* (2013.01);
(Continued)

(58) Field of Classification Search
CPC ............ A61B 5/02108; A61B 5/02141; A61B 5/02225; A61B 5/02233; A61B 5/6824;
(Continued)

(56) References Cited

U.S. PATENT DOCUMENTS

| | | | | |
|---|---|---|---|---|
| 8,075,493 | B2 * | 12/2011 | Kishimoto | ............. A61B 5/022 137/355.16 |
| 11,638,531 | B2 * | 5/2023 | Nishida | ................ A61B 5/0225 600/492 |

(Continued)

FOREIGN PATENT DOCUMENTS

| | | |
|---|---|---|
| CN | 103349546 A | 10/2013 |
| CN | 105940445 B | 6/2018 |

(Continued)

OTHER PUBLICATIONS

LOKMAT s6 smartwatch—Blood Pressure Airbag on your Wrist (Year: 2022).*
(Continued)

*Primary Examiner* — May A Abouelela
(74) *Attorney, Agent, or Firm* — Fish & Richardson P.C.

(57) ABSTRACT

One example blood pressure measurement device includes a body, a wrist strap, an airbag, an air supply and exhaust apparatus, a first sensor, and a second sensor. The airbag has an air cavity, and the airbag is connected to the body. The body includes a cavity, and the air supply and exhaust apparatus is disposed in the cavity. The air supply and exhaust apparatus includes an air intake path and an air exhaust path, and the air supply and exhaust apparatus communicates with the air cavity of the air bag. The first sensor is configured to measure an air pressure value in the air cavity. The second sensor is located on a same side of the wrist strap as the airbag, and is configured to measure a pulse wave signal.

20 Claims, 13 Drawing Sheets

(52) U.S. Cl.
CPC ........ *A61B 5/02233* (2013.01); *A61B 5/6824* (2013.01); *A61B 5/6831* (2013.01); *A61B 2560/0443* (2013.01); *A61B 2560/0462* (2013.01); *A61B 2562/0247* (2013.01); *A61B 2562/227* (2013.01)

(58) Field of Classification Search
CPC .......... A61B 5/6831; A61B 2560/0443; A61B 2560/0462; A61B 2562/0247; A61B 2562/227; A61B 5/02125; A61B 5/02416; A61B 5/681; A61B 5/0225; A61B 5/02438
See application file for complete search history.

(56) References Cited

U.S. PATENT DOCUMENTS

| | | | |
|---|---|---|---|
| 2003/0055347 A1 | 3/2003 | Itonaga et al. | |
| 2006/0058689 A1* | 3/2006 | Kishimoto | A61B 5/02233 600/490 |
| 2006/0195035 A1* | 8/2006 | Sun | A61B 5/022 600/503 |
| 2010/0010357 A1* | 1/2010 | Ostrowiecki | A61B 5/02233 600/499 |
| 2011/0054330 A1* | 3/2011 | Pfeiffer | A61B 5/02233 600/490 |
| 2013/0190576 A1* | 7/2013 | Matsumura | A61B 5/0235 600/301 |
| 2019/0209030 A1* | 7/2019 | Shimuta | A61B 5/02125 |
| 2019/0261870 A1 | 8/2019 | Nishikawa | |

| | | | |
|---|---|---|---|
| 2020/0077961 A1* | 3/2020 | Choi | A61B 5/486 |
| 2020/0321793 A1* | 10/2020 | Al-Ali | A61B 5/02438 |
| 2020/0323441 A1* | 10/2020 | Deno | A61B 5/0225 |
| 2021/0059544 A1* | 3/2021 | Nakagawa | A61B 5/4893 |
| 2021/0290086 A1* | 9/2021 | Nishida | A61B 5/6824 |
| 2021/0307626 A1* | 10/2021 | Ono | A61B 5/02141 |
| 2021/0308954 A1 | 10/2021 | Sano et al. | |
| 2023/0070636 A1* | 3/2023 | Kang | A61B 5/02116 |
| 2023/0200731 A1* | 6/2023 | Park | A61B 5/02108 |

FOREIGN PATENT DOCUMENTS

| | | | | |
|---|---|---|---|---|
| CN | 109803572 A | 5/2019 | | |
| CN | 105264680 B | 11/2019 | | |
| CN | 209863803 U | 12/2019 | | |
| CN | 111065323 A | 4/2020 | | |
| CN | 112472057 A | 3/2021 | | |
| CN | 112754438 A | 5/2021 | | |
| CN | 113520357 A | 10/2021 | | |
| EP | 1568313 A1 * | 8/2005 | ........ A61B 5/02233 |
| WO | WO-2022260398 A1 * | 12/2022 | ............ A61B 5/681 |
| WO | WO-2023103805 A1 * | 6/2023 | .......... A61B 5/6831 |

OTHER PUBLICATIONS

International Search Report and Written Opinion in International Appln. No. PCT/CN2022/134174, mailed on Feb. 23, 2023, 16 pages (with English translation).
Extended European Search Report in European Appln. No. 22903228.9, mailed on Feb. 3, 2025, 66 pages.

* cited by examiner

BLOOD PRESSURE MEASUREMENT DEVICE

CROSS-REFERENCE TO RELATED APPLICATIONS

This application is a national stage of International Application No. PCT/CN2022/134174, filed on Nov. 24, 2022, which claims priority to Chinese Patent application No. 202111477107.1, filed on Dec. 6, 2021. Both of the aforementioned applications are hereby incorporated by reference in their entireties.

TECHNICAL FIELD

This application relates to the field of electronic device technologies, and in particular, to a blood pressure measurement device.

BACKGROUND

Nowadays, people pay more attention to the health of themselves and their families, and blood pressure measurement is especially important. With the progress and development of science and technology, a blood pressure measurement device for home use appears, and a blood pressure measurement function is also integrated into some wearable devices (such as a smartwatch or a smart band) that each provide a possibility for a user to perform blood pressure measurement anytime and anywhere.

Currently, most blood pressure measurement devices commonly used in the industry perform blood pressure measurement by using oscillography. The oscillography features crowd statistics, and may have inaccurate individual measurement due to a problem of crowd adaptability. In addition, when an oscillographic blood pressure measurement device is used, a measurement error also increases as an age of a user under test increases. Moreover, the oscillography may also be applied to a dynamic blood pressure measurement device, and the oscillography may be used to perform 24-hour blood pressure monitoring on a patient, so that masked hypertension and nocturnal hypertension can be identified in a timely manner. This is more valuable to blood pressure measurement. However, the current dynamic blood pressure measurement device needs to put regular pressure. This causes severe uncomfortableness to a user, affects a life status of the user, and causes untrue measurement data.

Therefore, providing a blood pressure measurement device that can improve blood pressure measurement precision has become a difficult problem to be urgently resolved by a person skilled in the art.

SUMMARY

This application provides a blood pressure measurement device, to improve blood pressure measurement precision.

According to a first aspect, this application provides a blood pressure measurement device. The blood pressure measurement device may include a body, a wrist strap, an airbag, an air supply and exhaust apparatus, a first sensor, and a second sensor. The body includes a cavity, and the air supply and exhaust apparatus may be disposed in the cavity. The airbag may be connected to an end of the body, and the airbag has an air cavity. The air supply and exhaust apparatus may include an air intake path and an air exhaust path. The air supply and exhaust apparatus communicates with the air cavity of the airbag through the first air path. In this way, air enters the air supply and exhaust apparatus through the air intake path, and enters the air cavity of the airbag through a first air path, so as to implement air filling of the airbag. In addition, air in the airbag may be exhausted after passing through the first air path and the air exhaust path, so as to implement air exhausting of the airbag. The wrist strap may be connected to an end of the body, the second sensor is arranged on the wrist strap, and the second sensor is located on a same side of the wrist strap as the airbag. The first sensor may communicate with the air cavity of the airbag, to measure an air pressure value in the air cavity. The second sensor may be configured to measure a pulse wave signal. When the blood pressure measurement device is used to perform blood pressure measurement, the blood pressure measurement device may be worn on a wrist of the user. When the airbag is filled with air, the first sensor may be used to measure the air pressure value in the air cavity of the airbag. In this case, measurement of the air pressure value by the first sensor is not affected by the second sensor. In addition, because the second sensor is arranged on the wrist strap, even if the airbag is filled with air, measurement of the pulse xvave signal by the second sensor is not affected. Therefore, in a process of performing blood pressure measurement by using the blood pressure measurement device, measurement of the two sensors is independent of each other, and this can effectively improve measurement accuracy of the two sensors. In this way, after a relatively accurate air pressure value and a relatively accurate pulse wave signal are separately obtained, a relatively accurate blood pressure value may be obtained based on the air pressure value and the pulse wave signal.

When the airbag and the second sensor are arranged, in a possible implementation of this application, the airbag and the second sensor may be arranged side by side in a width direction of the wrist strap. In this way, arrangement of the second sensor can be effectively prevented from affecting measurement of the air pressure value by the first sensor, and impact on a measurement result of the second sensor when the airbag is in an air-filled state can be avoided, thereby helping improve measurement independence and accuracy of the first sensor and the second sensor.

In addition to the foregoing arrangement manner that can be used for the airbag and the second sensor, in another possible implementation of this application, the airbag and the second sensor may have a recess area. The recess area is not used to fill air, and may expose a part of the wrist strap. In this way, the second sensor may be located in the recess area, and may be connected to the wrist strap, so as to form an arrangement manner in which the airbag is arranged around the second sensor. It may be understood that, the arrangement manner can also effectively prevent arrangement of the second sensor from affecting measurement of the air pressure value by the first sensor, and can avoid impact on a measurement result of the second sensor when the airbag is in an air-filled state, thereby achieving an objective of independent measurement by the first sensor and the second sensor, and helping improve measurement accuracy of the blood pressure measurement device.

In a possible implementation of this application, when the airbag is specifically disposed, the airbag may include a hard support part and a flexible thin film part, where hardness of the hard support part is greater than hardness of the flexible thin film part. In this way, when the blood pressure measurement device is worn on the wrist, the hard support part may press the airbag toward the wrist, so as to ensure a fitting area between the airbag and the wrist, so that a relatively accurate blood pressure value can be obtained by measuring the air pressure value in the airbag by the first sensor.

In addition, in this application, the airbag may include at least two air chambers, the at least two air chambers are arranged in a stacked manner, and the at least two air chambers communicate. In this way, in a case of a same air filling volume, compared with an airbag including only one air chamber, a width of an airbag including two air chambers may be set to be relatively small, thereby facilitating implementation of a narrowing design of the entire airbag. Furthermore, because the airbag may be arranged on one side of the wrist strap, when a narrowing design of the airbag is implemented, it is convenient to design a relatively small width of the wrist strap. In this way, comfort of wearing the blood pressure measurement device can be effectively improved.

To better press-fit the airbag onto the wrist, the hard support part may be disposed at a connection portion between two adjacent air chambers. In addition, the fitting area between the airbag and the wrist may be adjusted by adjusting a disposed width of the hard support part, so as to improve reliability of the press-fitting between the airbag and the wrist.

In a possible implementation of this application, the airbag may include a first air chamber, a second air chamber, and a third air chamber. The second air chamber is located between the first air chamber and the third air chamber, the first air chamber may be connected to the wrist strap, and the second air chamber is separately connected to the first air chamber and the third air chamber. In addition, the first air chamber, the second air chamber, and the third air chamber communicate, and the hard support part may be disposed at a connection portion between the second air chamber and the third air chamber. It may be understood from the foregoing description of the airbag that the airbag includes the first air chamber, the second air chamber, and the third air chamber, and this may help implement a narrowing design of the airbag. The hard support part is disposed at the connection portion between the second air chamber and the third air chamber, so that the third air chamber can be effectively pressed toward the wrist. A fitting area between the third air chamber and the wrist may be adjusted by adjusting a disposed width of the hard support part. In this way, effective press-fitting between the airbag and the wrist is implemented.

In addition, an air volume of the third air chamber may be less than an air volume of the first air chamber, and the air volume of the third air chamber is less than an air volume of the second air chamber. In this way, the third air chamber may be filled with less air, so that there is a press force that meets a measurement requirement between the airbag and the wrist, and this helps improve measurement accuracy of the blood pressure measurement device.

Because wrist forms of different users are different, for example, wrists of some users are gradually widened in a direction from a palm to an elbow. To enable the airbag to adapt to use requirements of users having different wrist forms, in a possible implementation of this application, in a width direction of the airbag, the airbag may include a first edge and a second edge. When the blood pressure measurement device is worn on the wrist of the user, the first edge is disposed closer to the palm than the second edge. In addition, a minimum distance between the first edge and the connection portion is less than a minimum distance between the second edge and the connection portion, so that a requirement for fitting the airbag to the wrist can be met.

In this application, to implement connection between the airbag and the body, the body may have a connection hole, and the airbag is provided with an air nozzle. In this way, the airbag and the body may be connected by directly inserting the air nozzle into the connection hole. In addition, in another possible implementation of this application, the air nozzle of the airbag may further pass through the wrist strap and then be connected to the body. In this way, the airbag may be disposed at a relatively flexible position on the wrist strap, so that a same airbag can adapt to wrist straps with different wrist circumferences, and the airbag is applicable to a wider range of scenarios.

In a possible implementation of this application, the first sensor may be disposed in the cavity of the body, and the first sensor may communicate with the air cavity of the airbag through a second air path. In this case, the first sensor may be disposed in a differential pressure air pressure sensor, so that an air pressure value in the air cavity of the airbag can be measured.

In another possible implementation of this application, the first sensor may be disposed in the air cavity of the airbag. In this case, the first sensor may be an absolute pressure sensor or a differential pressure sensor. The first sensor is directly disposed in the air cavity, so that accuracy of measuring the air pressure value in the air cavity by the first sensor can be improved.

It may be understood that, to implement a measurement function of the first sensor and process the air pressure value measured by the first sensor, the first sensor usually needs to be electrically connected to a component such as a processor in the cavity of the body. Especially, when the first sensor is disposed in the air cavity of the airbag, the first sensor may be electrically connected to a component in the cavity of the body through an electrical connection cable. During specific implementation, the airbag has the air nozzle, and the airbag may be connected to the body through the air nozzle, Therefore, in a possible implementation of this application, a signal layer may be disposed on a surface of the air nozzle, a first electrical connection cable is electrically connected to the signal layer, and the signal layer is electrically connected to a component in the cavity of the body through a second electrical connection cable.

In addition, a plurality of types of signals may be transmitted between the first sensor and a component in the cavity of the body. On this basis, the signal layer may include a plurality of sub-signal layers, so that each sub-signal layer may be used to transmit one type of signal, thereby reducing crosstalk between different signals. For example, the signal layer may include a first sub-signal layer and a second sub-signal layer. In this case, the first sub-signal layer and the second sub-signal layer may be separately electrically connected to the first sensor through the first electrical connection cable, and the first sub-signal layer and the second sub-signal layer may be separately electrically connected to a component in the cavity through the second electrical connection cable. It should be noted that the first electrical connection cable and the second electrical connection cable may each include one cable, or may each include a group of cables formed by a plurality of cables, and may be specifically selected based on a to-be-transmitted signal.

In this application, the first sub-signal layer and the second sub-signal layer may be disposed on the air nozzle in a plurality of manners. For example, in a radial direction of the air nozzle, cross-sectional shapes of both the first sub-signal layer and the second sub-signal layer may be annular shapes, and the second sub-signal layer is sleeved around the first sub-signal layer. Alternatively, in a radial direction of the air nozzle, cross-sectional shapes of both the first sub-signal layer and the second sub-signal layer may be parts of annular shapes, and the first sub-signal layer and the second sub-signal layer are not connected to each other. In addition, to avoid a short circuit between the first sub-signal layer and the second sub-signal layer, an insulation layer may be disposed between the first sub-signal layer and the second sub-signal layer.

In another possible implementation of this application, the first sub-signal layer may include an annular portion disposed around an axial direction of the air nozzle, and a first extension portion disposed in the axial direction of the air nozzle. In addition, the second sub-signal layer may include a semi-annular portion disposed around the axial direction of the air nozzle and a second extension portion disposed in the axial direction of the air nozzle. In addition, the annular portion and the semi-annular portion are arranged in a staggered manner in the axial direction of the air nozzle.

In addition to a fact that the first sensor may be electrically connected to the component in the cavity of the body in the foregoing manner, it is considered that the airbag has the air nozzle, and the airbag may be connected to the body through the air nozzle. Therefore, in a possible implementation of this application, the first electrical connection cable connected to the first sensor may further extend into the cavity of the body after passing through the air nozzle, and the first electrical connection cable is electrically connected to a component in the cavity.

In a possible implementation of this application, the blood pressure measurement setting may further include a photoplethysmograph PPG module, and the PPG module may be disposed on a bottom surface of the body. In this way, the blood pressure value ma be obtained based on the air pressure value measured by the first sensor, the pulse wave signal measured by the second sensor, and/or a photoplethysmographic pulse wave signal measured by the PPG module.

In addition, in this application, the airbag is detachably connected to the body. In this way, after a relatively accurate blood pressure value is obtained by using the air pressure value measured by the first sensor and the pulse wave signal measured by the second sensor, the airbag may be detached. Then, continuous blood pressure measurement is implemented based on the foregoing obtained blood pressure value and based on pulse wave measurement performed by the second sensor. This can improve comfort of wearing by the user, thereby helping improve accuracy of the continuous blood pressure measurement.

According to a second aspect, this application further provides a blood pressure measurement device. The blood pressure measurement device may include a body, an airbag, an air supply and exhaust apparatus, a first sensor, and a second sensor. The body includes a cavity, and the air supply and exhaust apparatus may be disposed in the cavity. The airbag may be connected to an end of the body, and the airbag has an air cavity. The air supply and exhaust apparatus may include an air intake path and an air exhaust path. The air supply and exhaust apparatus communicates with the air cavity of the airbag through the first air path. In this way, air enters the air supply and exhaust apparatus through the air intake path, and enters the air cavity of the airbag through a first air path, so as to implement air filling of the airbag. In addition, air in the airbag may be exhausted after passing through the first air path and the air exhaust path, so as to implement air exhausting of the airbag. The first sensor communicates with the air cavity of the airbag, to measure an air pressure value in the air cavity, and a first blood pressure value may be obtained based on the air pressure value measured by the first sensor. In addition, when the airbag is not filled with air, the second sensor may obtain a pulse wave signal. On this basis, a second blood pressure value may be obtained based on the first blood pressure value and the pulse wave signal measured by the second sensor. Because the second sensor may measure the pulse wave signal continuously, the blood pressure measurement device in this embodiment may be used to implement continuous blood pressure measurement.

In a possible implementation of this application, the airbag may be detachably connected to an end of the body, and the airbag and the second sensor are arranged in a stacked manner. In this way, after the air pressure value in the airbag is measured and the first blood pressure value is obtained, the airbag may be detached from the body. This helps improve comfort of wearing the blood pressure measurement device, thereby reducing impact on a blood pressure fluctuation of a user, so that the second blood pressure value subsequently obtained based on the first blood pressure value and the pulse wave signal measured by the second sensor is relatively accurate.

In addition, generally, the blood pressure measurement device may further include a wrist strap, and the wrist strap may be connected to an end of the body. In a possible implementation of this application, the second sensor may be disposed on the wrist strap, and the second sensor is located between the airbag and the wrist strap, so that after the airbag is detached, the second sensor can measure the pulse wave signal.

In another possible implementation of this application, the second sensor may be disposed on a bottom surface of the body, and the second sensor may be a photoplethysmograph PPG module. In this way, when the PPG module is used to measure a heart rate, the second blood pressure value and the photoplethysmographic pulse wave signal measured by the PPG module may be further obtained based on the obtained first blood pressure value and the photoelectric volume pulse wave signal measured by the PPG module. The PPG module is reused, thereby improving integration of the blood pressure measurement device.

In another possible implementation of this application, the second sensor may be further disposed in the air cavity of the airbag, so that an appearance of the blood pressure measurement device is relatively simple. In addition, according to this design, when the air cavity of the airbag can be filled with air, the first blood pressure value may be obtained by measuring the air pressure value in the air cavity by using the first sensor, and when the air cavity is not filled with air, the second sensor can be fitted to the wrist to measure the pulse wave signal, so that it is convenient to use the blood pressure measurement device.

REFERENCE NUMERALS

1: body; 101: cavity; 102: connection hole; 2: airbag; 201: recess area; 202: air nozzle; 203: hard support part; 204: flexible thin film part; 2041: first layer structure; 2042: second layer structure; 2043: third layer structure; 205: air hole;

206: first air chamber; 207: second air chamber; 208: third air chamber; 209: first edge; 210: second edge; 3: wrist strap;

4: first sensor; 5: second sensor; 6: air path cavity; 7: air path; 8: air path; 9: air supply and exhaust apparatus; 10: air path.

11: drive apparatus; 12: processor; 13: drive circuit; 14: PPG module; 15: ECG detection module; 16: first air valve;

17: second air valve; 18: first electrical connection cable; 19: signal layer; 1901: first sub-signal layer; 1902: second sub-signal layer; 20: insulation layer; 21: protective layer.

DESCRIPTION OF EMBODIMENTS

To make the objectives, technical solutions, and advantages of this application clearer, the following further describes this application in detail with reference to the accompanying drawings.

To facilitate understanding of a blood pressure measurement device provided in embodiments of this application, the following first describes an application scenario of the blood pressure measurement device. The blood pressure measurement device may be, but is not limited to, a device with a relatively large volume and used for blood pressure measurement, such as a medical device or a household device, or may be a portable electronic device with a blood pressure measurement function, such as a smartwatch or a smart band. A smartwatch is used as an example. The smartwatch may be worn on a wrist of a user, so as to detect a physical sign such as a blood pressure of the user at any time, to predict a state of health, thereby effectively avoiding a dangerous secondary disease such as a stroke caused by hypertension.

Figure 1:
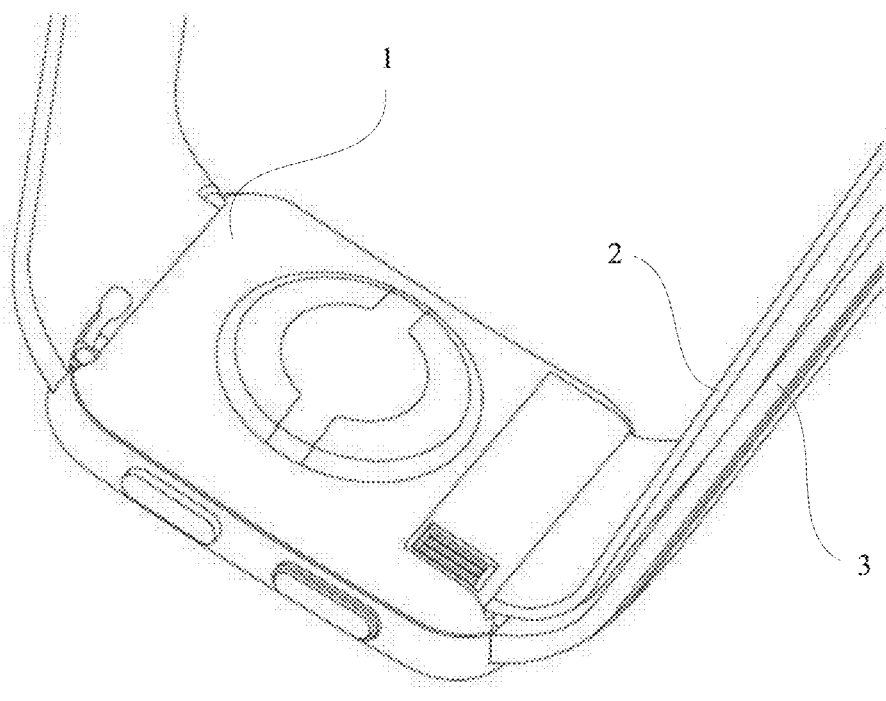
FIG. 1 is a diagram of a structure of a smartwatch with a blood pressure measurement function according to an embodiment of this application.

FIG. 1 is a diagram of a structure of a smartwatch with a blood pressure measurement function according to an embodiment of this application. The smartwatch may include a body 1 and an airbag 2, and the airbag 2 may be fastened to an end of the body 1. For example, the airbag 2 may be fastened to an end of a bottom surface of the body 1. In this application, the bottom surface of the body 1 is a surface that is of the body 1 and that is directly in contact with the wrist when the smartwatch is worn on the wrist. In addition, the blood pressure measurement device may further include a wrist strap 3. As shown in FIG. 1, the airbag 2 may be located on a side that is of the wrist strap 3 and that faces the user. In this way, when the wrist strap 3 is wrapped around the wrist of the user, the airbag 2 may be pressed toward the wrist, so that the airbag 2 is fitted to the wrist, thereby facilitating blood pressure measurement of the user. It may be understood that, the airbag 2 and the wrist strap 3 may be fastened in a manner of clamping, bonding, or riveting, to reduce friction generated by mutual movement between the airbag 2 and the wrist strap 3, thereby reducing a risk of wear of the airbag 2 and improving a service life of the blood pressure measurement device.

Currently, most blood pressure measurement devices commonly used in the industry perform blood pressure measurement based on a principle of oscillography. The oscillography features crowd statistics, and this may have inaccurate individual measurement due to a problem of crowd adaptability. In addition, the blood pressure measurement device based on the principle of the oscillography has a measurement error increasing as an age of a user under test increases. In addition, in addition to a blood pressure measurement device that performs a single blood pressure measurement on a user based on a principle of the oscillography, some blood pressure measurement devices used for dynamic blood pressure measurement also work based on the principle of the oscillography, to implement 24-hour uninterrupted blood pressure monitoring, so that masked hypertension and nocturnal hypertension can be effectively identified. This has higher application value in blood pressure measurement. However, a current device that can be used for dynamic blood pressure measurement needs to put regular pressure on a user. This causes severe uncomfortable feeling to the user, affects a life status of the user, and easily causes untrue blood pressure measurement data.

In addition, a conventional mercury stethoscope is a blood pressure measurement device that performs blood pressure measurement based on a Korotkoff-Sound method. The conventional mercury stethoscope does not feature crowd statistics, and is a relatively reliable measurement device in the field of medical and human blood pressure measurement, so that the conventional mercury stethoscope is universally used and internationally recognized. However, the conventional mercury stethoscope is being withdrawn from the market due to inconvenient operation and mercury pollution.

On this basis, an embodiment of this application provides a blood pressure measurement device. The blood pressure measurement device improves blood pressure measurement precision through mutual calibration between measurement data of a plurality of sensors, so that cardiovascular disease prevention and treatment can be improved by accurately measuring a blood pressure. For ease of understanding, in the following embodiments of this application, a specific structure of the blood pressure measurement device is described in detail by using a smartwatch as an example.

Terms used in the following embodiments are merely intended to describe specific embodiments, and are not intended to limit this application. Terms "one", "a", "the foregoing", "the", and "the one" of singular forms used in this specification and the appended claims of this application are also intended to include plural forms like "one or more", unless otherwise specified in the context clearly. It should be further understood that in the following embodiments of this application, "at least one" and "one or more" refer to one, two, or more. The term "and/or" is used for describing an association relationship between associated objects, and indicates that three relationships may exist. For example, A and/or B may represent: Only A exists, both A and B exist, and only B exists, where A and B may be singular or plural. The character "/" generally indicates an "or" relationship between the associated objects.

Reference to "one embodiment" or "some embodiments" described in this specification means that a specific characteristic, structure or feature described in combination with this embodiment is included in one or more embodiments of this application. Therefore, statements "in one embodiment", "in some embodiments", "in some other embodiments", "in other embodiments", and the like in the differences in this specification do not necessarily refer to the same embodiment, but mean "one or more but not all embodiments", unless otherwise specially emphasized in other ways. Terms "include", "comprise". "have", and variations thereof all mean "including but not limited to", unless otherwise specified.

Figure 2:
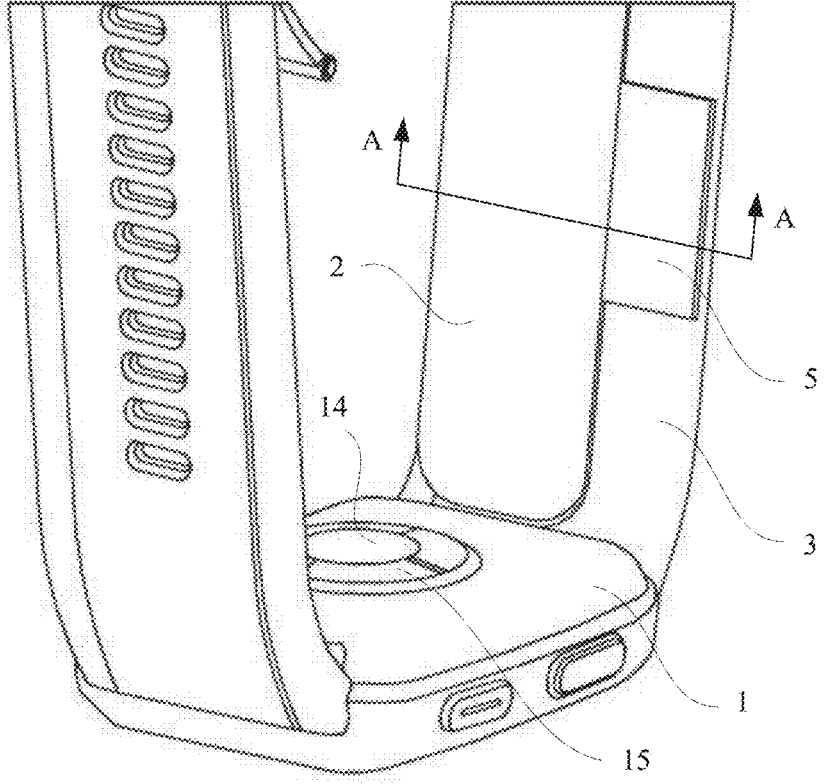
FIG. 2 is a diagram of a structure of a blood pressure measurement device according to an embodiment of this application.

FIG. 2 is a diagram of a structure of a blood pressure measurement device according to a possible embodiment of this application. In this embodiment of this application, the blood pressure measurement device may include a body 1 and an airbag 2. The body 1 has a cavity, and main functional modules and components of the blood pressure measurement device may be disposed in the cavity. In this application, the airbag 2 may be connected to an end of the body 1, the airbag 2 may have an air cavity, and the air cavity of the airbag 2 may communicate with the cavity of the body 1.

In this application, the blood pressure measurement device may further include a first sensor (not shown in FIG. 2) and a second sensor 5. The first sensor may communicate with the air cavity of the airbag 2, to measure an air pressure value in the air cavity. The second sensor 5 may be configured to measure a pulse wave signal. Still refer to FIG. 2. The second sensor 5 may be disposed on one side of the airbag 2. The second sensor 5 may be a pulse wave sensor, and may be configured to measure pulse wave signal data of a pulse on one side of the airbag 2. In this application, a specific type of the second sensor 5 is not limited. For example, the second sensor 5 may be a laser microphone sensor. In a process of putting pressure on the wrist of the user by using the airbag 2, the second sensor 5 may pick up a tiny sound signal generated when a blood vessel is under the impact of a blood flow, and process the tiny sound signal to obtain a pulse wave signal. In addition, the second sensor 5 may be further a sensor module or the like.

Moreover, the blood pressure measurement device may further include a wrist strap 3, and the wrist strap 3 is connected to an end of the body 1. Both the airbag 2 and the second sensor 5 may be located on a side that is of the wrist strap 3 and that faces the wrist of the user, and the second sensor 5 is disposed on the wrist strap 3. Therefore, when the wrist strap 3 is worn on the wrist, the airbag 2 and the second sensor 5 may be pressed toward the wrist, so that the airbag 2 and the second sensor 5 can be fitted to the wrist, thereby implementing blood pressure measurement. In the embodiment shown in FIG. 2, in a width direction of the wrist strap 3, the airbag 2 and the second sensor 5 may be arranged side by side on the wrist strap 3. In this way, when the airbag 2 is filled with air, the first sensor may measure the air pressure value in the air cavity of the airbag 2. In this case, measurement of the air pressure value by the first sensor is not affected by the second sensor 5. In addition, because the second sensor 5 and the airbag 2 are arranged side by side on the wrist strap 3, even if the airbag 2 is filled with air, measurement of a pulse wave by the second sensor 5 is not affected by airbag filling. Therefore, measurement of the two sensors is independent of each other, and this can effectively improve measurement accuracy of the two sensors. It should be noted that, in this application, a structure size of the wrist strap 3 in a direction from a palm to an elbow may be defined as a width of the wrist strap 3, and a length of the wrist strap 3 may be defined as a structure size of the wrist strap 3 in a direction around the wrist.

Figure 3:
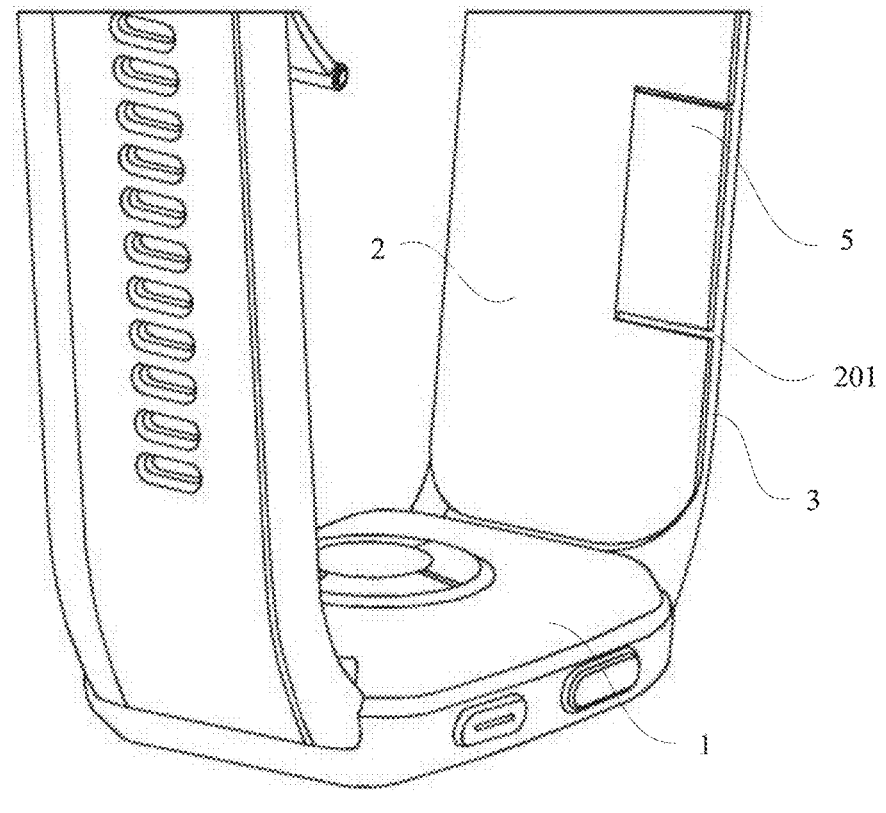
FIG. 3 is a diagram of a structure of a blood pressure measurement device according to another embodiment of this application.

FIG. 3 is a diagram of a structure of a blood pressure measurement device according to another possible embodiment of this application. In the embodiment shown in FIG. 3, a recess area 201 is disposed on the airbag 2. The recess area 201 is not used to fill air, and may expose a part of the wrist strap. In this way, the second sensor 5 may be accommodated in the recess area 201 and disposed on the wrist strap 3. In this embodiment, in the width direction of the wrist strap 3, a size of the airbag 2 is relatively large. This may help increase an effective contact area between the airbag 2 and the wrist. Therefore, when the airbag 2 is filled with air, effective extrusion can be performed on the wrist, to improve accuracy of blood pressure measurement. In addition, that the arrangement manner in this embodiment is used for the airbag 2 and the second sensor 5 can also effectively prevent arrangement of the second sensor 5 from affecting a measurement result of the air pressure value by the first sensor 4, and can avoid impact on a measurement result of the second sensor 5 when the airbag is in an air-filled state, thereby achieving an objective of independent measurement by the first sensor 4 and the second sensor 5, and helping improve measurement accuracy of the blood pressure measurement device.

It may be understood that, in the embodiment shown in FIG. 2 or FIG. 3, a manner of disposing the airbag 2 and the second sensor 5 is merely an example description provided in this application. In addition, the airbag 2 and the second sensor 5 may be alternatively disposed in another possible manner. However, regardless of a manner in which the airbag 2 and the second sensor 5 are disposed, in the width direction of the wrist strap 3, a sum of sizes of the airbag 2 and the second sensor 5 may be less than or equal to the width of the wrist strap 3. In this way, when the wrist strap 3 can press the airbag 2 and the second sensor 5 toward the wrist, the wrist strap 3 can further protect the airbag 2 and the second sensor 5.

Figure 4:
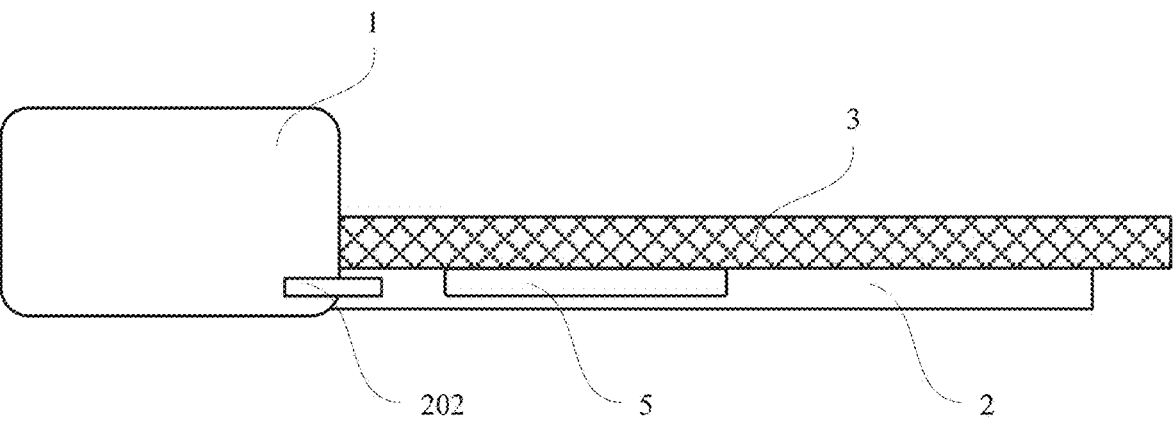
FIG. 4 is a block diagram of a structure of connection between an airbag and a body according to an embodiment of this application.
Figure 5:
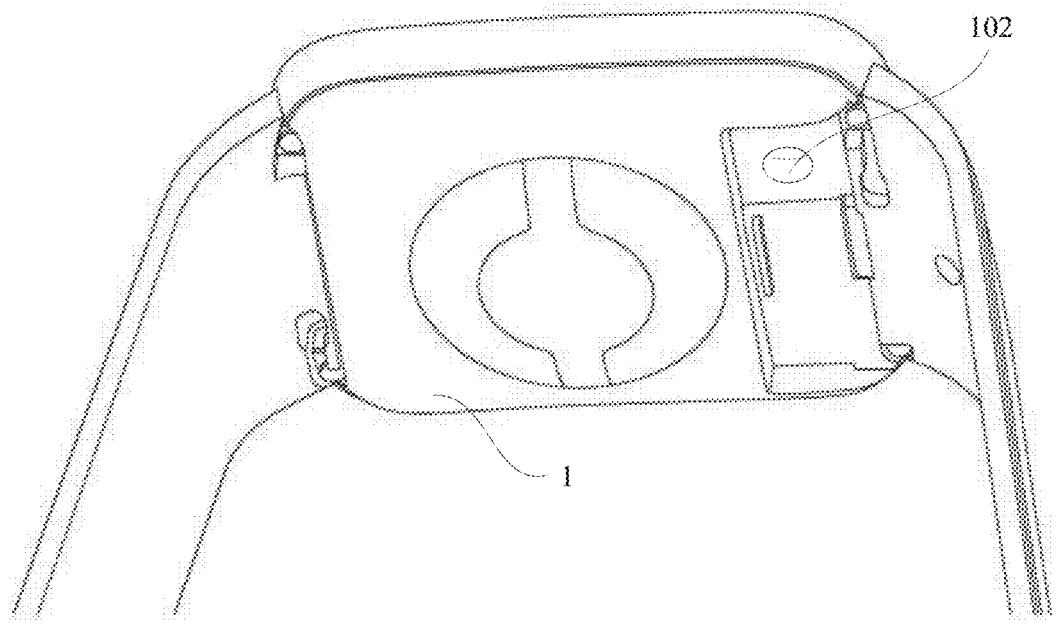
FIG. 5 is a diagram of a structure of a body according to an embodiment of this application.
Figure 6:
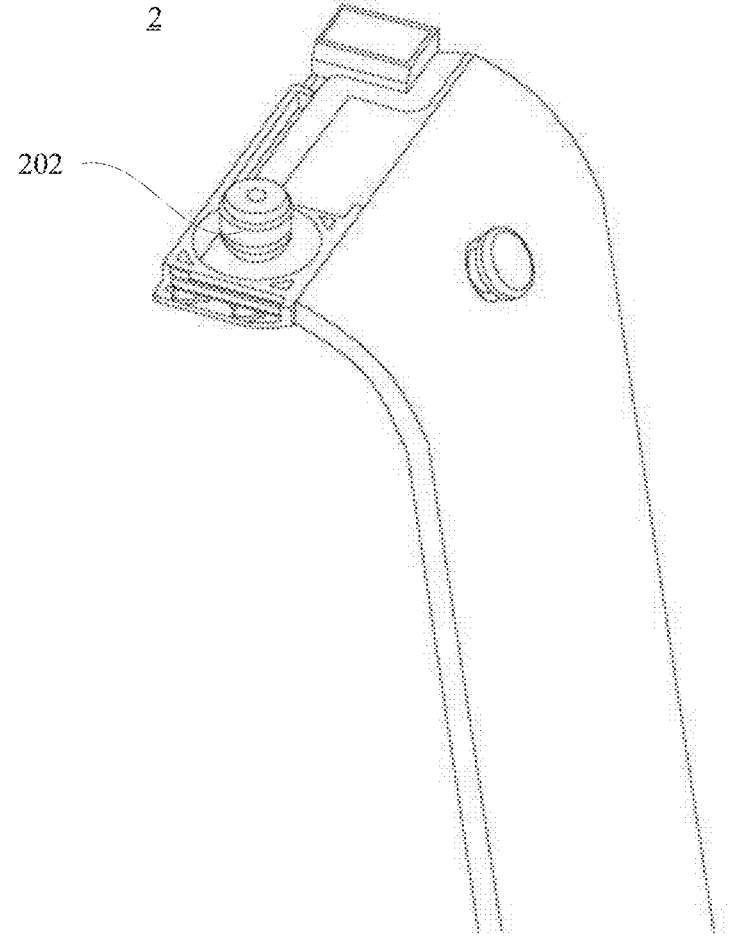
FIG. 6 is a diagram of a structure of an airbag according to an embodiment of this application.

In this application, to implement communication between the air cavity of the airbag 2 and the cavity 101 of the body 1, refer to FIG. 4. FIG. 4 is a block diagram of a structure of connection between the airbag 2 and the body 1 according to a possible embodiment of this application. In this embodiment, the airbag 2 may be directly connected to the body 1 through an air nozzle 202. During specific implementation, refer to FIG. 5. FIG. 5 is a diagram of a structure of the body 1 according to a possible embodiment of this application. In this embodiment, a bottom surface of the body 1 may be provided with a connection hole 102 for connecting to the airbag 2. In addition, refer to FIG. 6. FIG. 6 is a diagram of a structure of the airbag 2 according to a possible embodiment of this application. In this embodiment, the airbag 2 may be provided with an air nozzle 202, and the air nozzle 202 may be inserted into the connection hole 102 of the body 1 shown in FIG. 5, so as to implement communication between the air cavity of the airbag 2 and the cavity 101 of the body 1.

In the embodiments shown in FIG. 5 and FIG. 6, the airbag 2 is connected to one connection hole 102 of the body 1 by using one air nozzle 202. This can effectively reduce a quantity of provided connection holes 102 of the body 1 of the blood pressure measurement device, to improve overall sealing performance of the blood pressure measurement device. This can reduce a risk of damage to a functional module and a component in the cavity 101 of the body 1 of the blood pressure measurement device, thereby helping prolong a service life of the blood pressure measurement device.

In addition in this embodiment of this application, a specific structure of the air nozzle 202 is not limited. For example, still refer to FIG. 6. The air nozzle 202 may protrude from the airbag 2 through a side surface of the airbag 2 in a direction toward the body 1. In this way, the airbag 2 may be fixedly connected to the body 1 by inserting the air nozzle 202 into the connection hole 102. In some other possible embodiments of this application, the air nozzle 202 may be further disposed on the body 1, and the connection hole 102 is disposed on the airbag 2. In this case, the body 1 and the airbag 2 may also be connected by inserting the air nozzle 202 into the connection hole 102. It should be noted that a structure (the air nozzle 202 or the connection hole 102) that is on the body 1 and that is used to connect to the airbag 2 may be disposed on the bottom surface of the body 1 shown in FIG. 5, or may be disposed on any side surface of the body 1. This is not specifically limited in this application.

Figure 7:
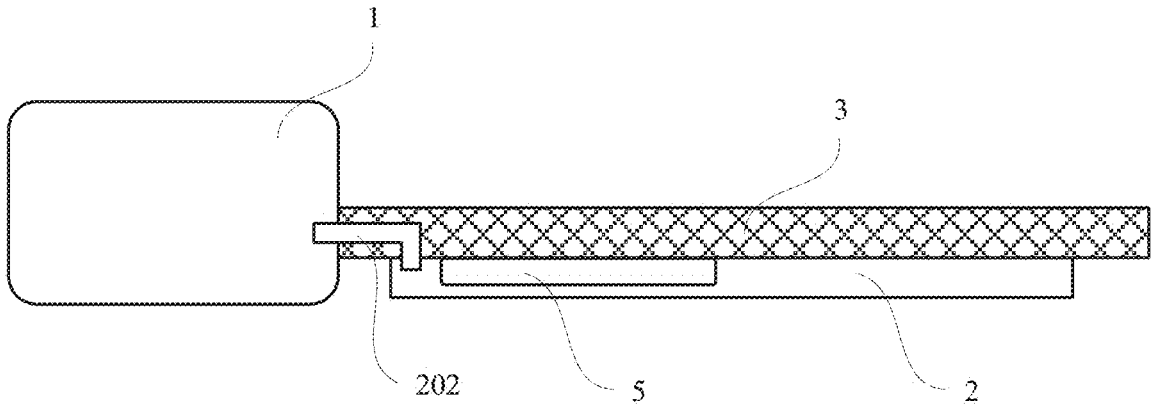
FIG. 7 is a block diagram of a structure of connection between an airbag and a body according to another embodiment of this application.

In this application, the airbag 2 may be directly connected to the body 1 by using the air nozzle 202. In addition, in some possible embodiments of this application, the airbag 2 may be indirectly connected to the body 1. During specific implementation, refer to FIG. 7. FIG. 7 is a block diagram of a structure of connection between the airbag 2 and the body 1 according to another possible embodiment of this application. In this embodiment, the air nozzle 202 may be inserted into the connection hole 102 after passing through the wrist strap 3, so as to implement connection between the airbag 2 and the body 1. In this way, the wrist strap 3 can protect the air nozzle 202. In addition, the airbag 2 may be disposed at a relatively flexible position on the wrist strap 3, so that a same airbag 2 can adapt to wrist straps 3 with different wrist circumferences, and the airbag 2 is applicable to a wider range of scenarios.

Figure 8:
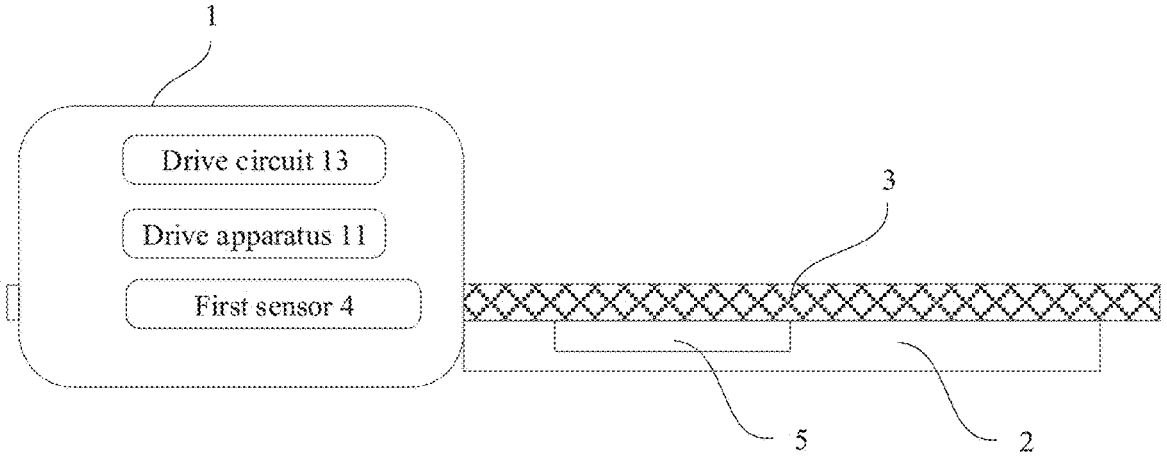
FIG. 8 is a block diagram of a structure of a blood pressure measurement device according to an embodiment of this application.

In a possible embodiment of this application, when the first sensor 4 is specifically disposed, the first sensor 4 may be an air pressure sensor, and may communicate with the air cavity of the airbag 2, to measure an air pressure value in the air cavity of the airbag 2. In this application, a specific disposing position of the first sensor 4 is not limited. In a possible embodiment of this application, the first sensor 4 may be disposed in the cavity 101 of the body 1. During specific implementation, refer to FIG. 8. FIG. 8 is a block diagram of a structure of the blood pressure measurement device according to another possible embodiment of this application. In this embodiment, the first sensor 4 may be but is not limited to a differential pressure air pressure sensor.

Figure 9:
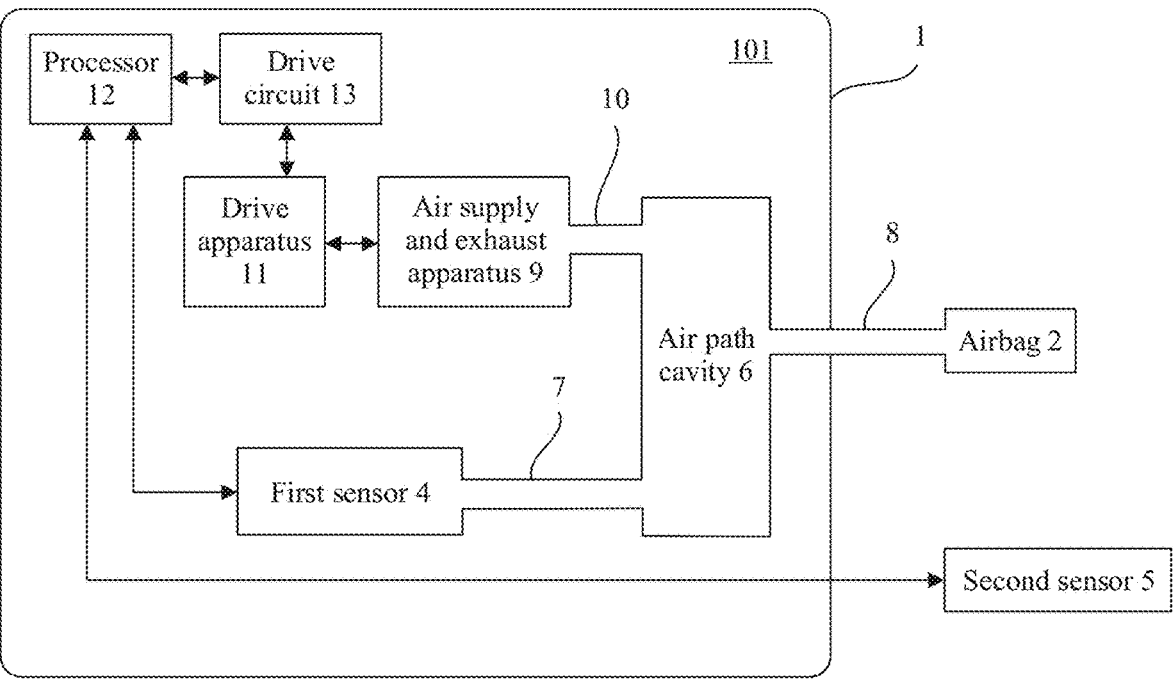
FIG. 9 is a block diagram of a structure of a blood pressure measurement device according to another embodiment of this application.

In addition, the first sensor 4 may communicate with the air cavity of the airbag 2 through an air path, so that an air pressure value in the airbag 2 can be measured in a blood pressure measurement process. During specific implementation, refer to FIG. 9. FIG. 9 is a block diagram of a structure of the blood pressure measurement device according to another possible implementation of this application. It should be noted that, in the embodiment shown in FIG. 9, a straight line or a broken line with double arrows is used to represent an electrical connection cable. Each straight line or broken line with double arrows may represent one or more transmission lines. This is not limited in this application. In addition, in FIG. 9, a doubly straight line is used to represent air path connection.

Still refer to FIG. 9. In this embodiment, the blood pressure measurement device may further include an air path cavity 6, and the air path cavity 6 may be disposed in the cavity 101 of the body 1. In addition, the air path cavity 6 may be fastened to a side wall of the body 1 through bonding or threaded connection, thereby improving structural stability of the air path cavity 6. The first sensor 4 may communicate with the air path cavity 6 through an air path 7, and the airbag 2 may communicate with the air path cavity 6 through an air path 8, so that the first sensor 4 can collect the air pressure value in the airbag 2.

To adjust the air pressure value in the airbag 2, in this application, the blood pressure measurement device may further include an air supply and exhaust apparatus 9. The air supply and exhaust apparatus 9 may be disposed in the cavity 101 of the body 1, and the air supply and exhaust apparatus 9 may include an air intake path (not shown in FIG. 9) and an air exhaust path (not shown in FIG. 9). In addition, the air supply and exhaust apparatus 9 may communicate with the air path cavity 6 through an air path 10. In this way, air may enter the air supply and exhaust apparatus 9 through the air intake path, and enter the airbag 2 through the air path 10, so that the air supply and exhaust apparatus 9 implements air filling of the airbag 2. Conversely, when air in the airbag 2 needs to be exhausted, the air exhaust and supply apparatus 9 extracts the air in the airbag 2 through the air path 10, and exhausts the air through the air exhaust path.

In this application, a specific structure of the air supply and exhaust apparatus 9 is not limited. For example, the air supply and exhaust apparatus 9 may be an air pump, and a volume of the air pump may be set based on a requirement of the airbag 2 of the blood pressure measurement apparatus for air supply and exhaust and a space size of the cavity 101 of the body 1.

Still refer to FIG. 9. The blood pressure measurement device may further include a drive apparatus 11, and the drive apparatus 11 may be electrically connected to the air supply and exhaust apparatus 9. The drive apparatus 11 may be configured to provide a driving force for an air filling and exhausting process of the air supply and exhaust apparatus 9. In this application, the drive apparatus 11 is not specifically limited either, and may be, for example, a motor or the like. In addition, a value of a driving force provided by the drive apparatus 11 for the air supply and exhaust apparatus 9 may be implemented by controlling, by a processor 12 in the body 1 of the blood pressure measurement device, the drive circuit 13 electrically connected to the drive apparatus 11.

According to the blood pressure measurement device provided in this embodiment of this application, the air path cavity 6 is disposed, so that after being connected to the air supply and exhaust apparatus 9 through the air path cavity 6, the first sensor 4 may be connected to the air cavity of the airbag 2 through one air path (that is, the air path 8), and the airbag 2 can be connected to a single air nozzle of the body 1.

Figure 10A:
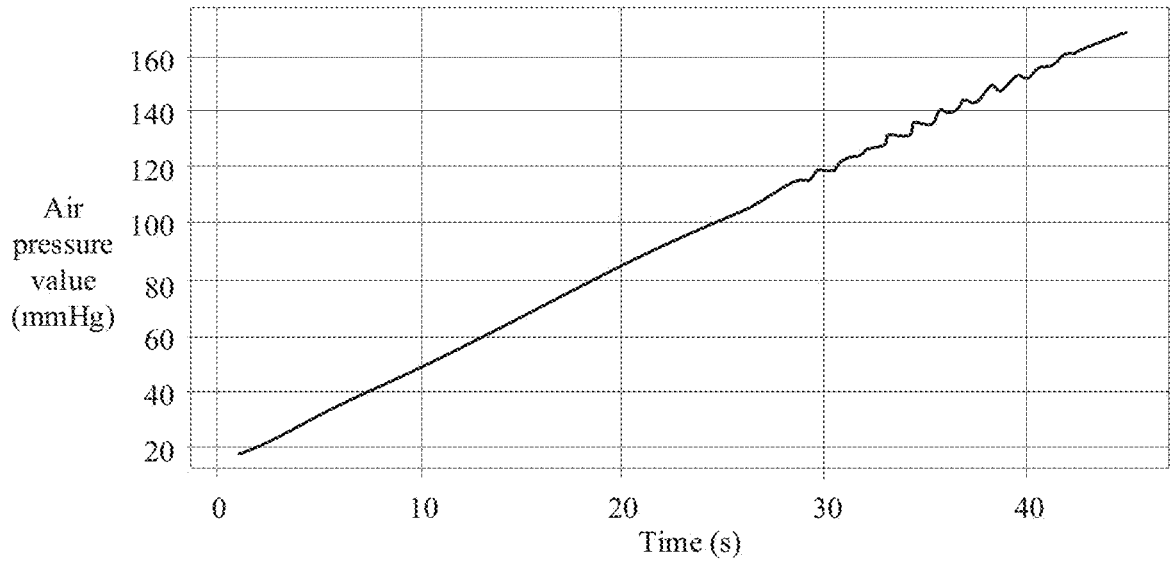
FIG. 10a to FIG. 10c are waveform diagrams of air pressure values, in an airbag, collected by a first sensor according to an embodiment of this application.

Still refer to FIG. 9. In this application, the second sensor 5 may be alternatively electrically connected to the processor 12 in the body 1 of the blood pressure measurement device, to control a measurement process of the second sensor 5 by using the processor 12. By using the blood pressure measurement device provided in this application, the air pressure value in the airbag 2 may be collected by using the first sensor 4. In addition, the pulse wave signal collected by the second sensor 5 may be used to calibrate a blood pressure value obtained based on the air pressure value, in the airbag 2, collected by the first sensor 4. A specific step of obtaining a human blood pressure value by using the first sensor 4 and the second sensor 5 may be as follows: First, the first sensor 4 collects the air pressure value in the airbag 2. Refer to FIG. 1a FIG. 10a is a waveform diagram of the air pressure value, in the airbag 2, collected by the first sensor 4 according to an embodiment of this application, A first blood pressure value BP1 may be obtained by processing the air pressure value, in the airbag 2, collected by the first sensor 4, where BP1=h(P), and P is the air pressure value in the airbag 2. It should be noted that in this application, the blood pressure value BP may be a systolic blood pressure (systolic blood pressure, SBP), or may be a diastolic blood pressure (diastole pressure, DBP). In other words, the first blood pressure value BP1 may be a first systolic blood pressure SBP1, or may be a first diastolic blood pressure DBP1. In addition, a method for obtaining the first blood pressure value BP1 based on the air pressure value, in the airbag 2, collected by the first sensor 4 is similar to oscillography A method for obtaining a blood pressure value by using the oscillography is a relatively mature technology in the art, and details are not described in this application.

Figure 10B:
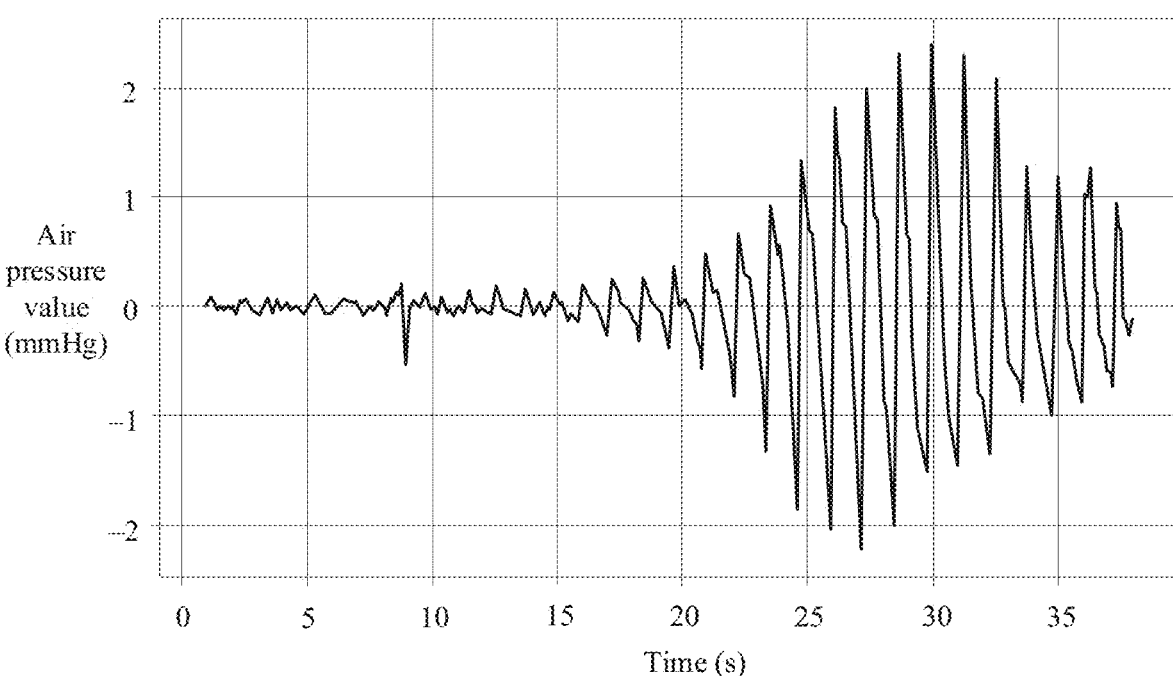
Figure 10C:
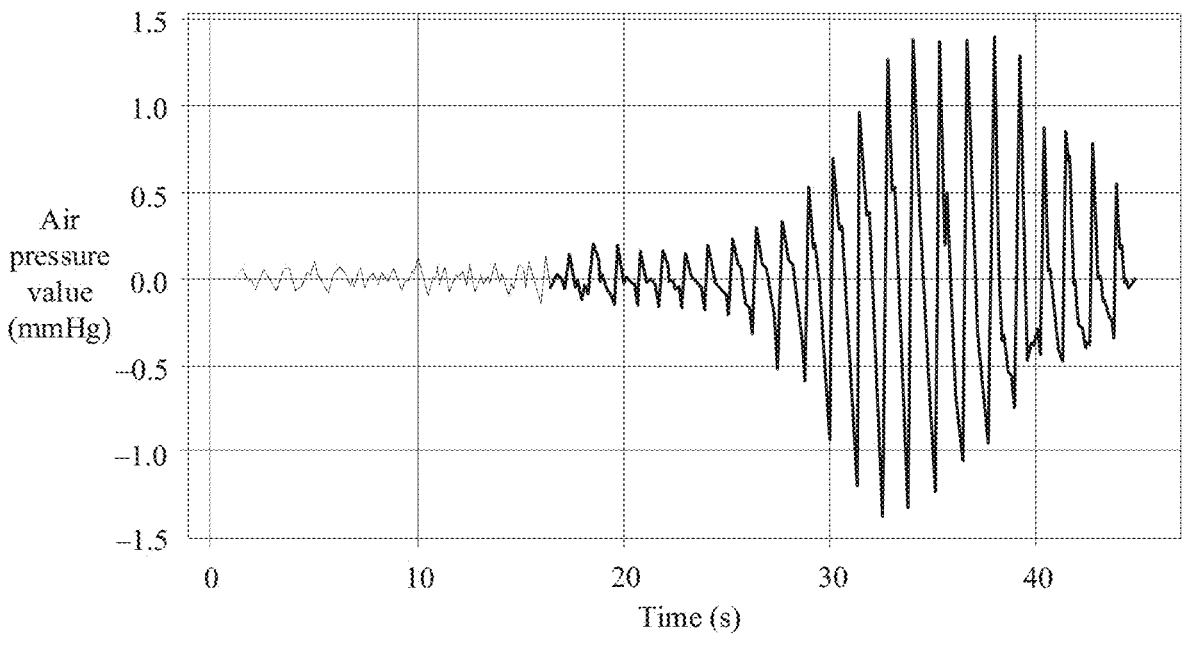

It may be understood that FIG. 10a is merely an example description of a waveform of the air pressure value collected by the first sensor 4 in this application. In some other possible embodiments of this application, the waveform of the air pressure value collected by the first sensor 4 may be alternatively in another form. For example, refer to FIG. 10b and FIG. 10c. FIG. 10b and FIG. 10c are waveform diagrams of air pressure values, in the airbag 2, collected by the first sensor 4 according to another embodiment of this application.

Figure 11A:
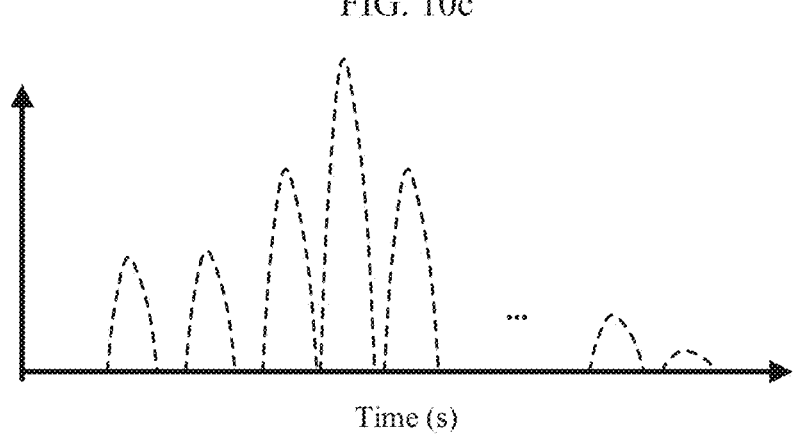
FIG. 11a and FIG. 11b are waveform diagrams of pulse wave signals collected by a second sensor according to an embodiment of this application.

Then, the second sensor 5 collects a pulse wave signal of a human body. Refer to FIG. 11a. FIG. 11a is a waveform diagram of the pulse wave signal collected by the second sensor 5 according to an embodiment of this application. In FIG. 11a, a vertical coordinate of FIG. 11a represents a normalized signal amplitude. In this application, a second blood pressure value BP2 may be obtained by processing the pulse wave signal collected by the second sensor 5, where BP2=f(P), and P is an air pressure value in the airbag 2. It should be noted that in this application, the second blood pressure value BP2 may be a second systolic blood pressure SBP2, or may be a second diastolic blood pressure DBP2. In addition, a method for collecting the pulse wave signal by using the second sensor 5, and obtaining the second blood pressure value BP2 based on the pulse wave signal is similar to a stethoscopy method or a waveform method. A method for obtaining a blood pressure value by using the stethoscopy method or the waveform method is a relatively mature technology in the art, and details are not described in this application.

Figure 11B:
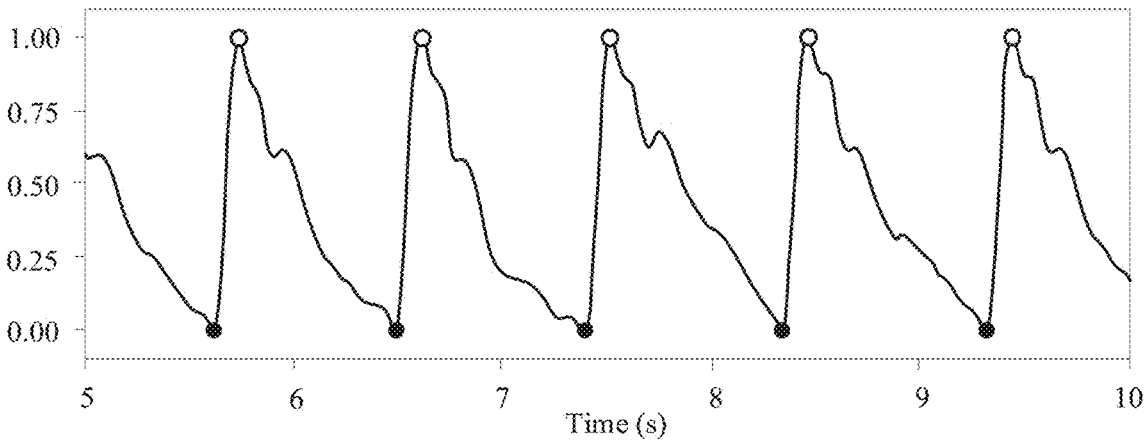

It may be understood that FIG. 11a is merely an example description of a waveform of a pulse wave collected by the second sensor 5 in this application. In some other possible embodiments of this application, the waveform of the pulse wave collected by the second sensor 5 may be alternatively in another form. For example, refer to FIG. 11b. FIG. 11b is a waveform diagram of the pulse wave signal collected by the second sensor 5 according to another embodiment of this application.

Finally, the blood pressure value BP of the human body may be obtained based on a mapping relationship between the first blood pressure value BP1 and the second blood pressure value BP2, and BP=H(BP1)+F(BP2), where F and H are relational expressions obtained through analysis based on a big data fitting function.

In this way, according to the blood pressure measurement device provided in this application, a pulse wave signal on one side of the airbag 2 can be collected when the airbag 2 presses a blood vessel and performs blood pressure measurement by using the oscillography, so that a change feature of a physiological signal in a process of pressing the blood vessel can be obtained. Therefore, the blood pressure value of the human body may be obtained with reference to the air pressure value, in the airbag 2, collected by the first sensor 4 and the pulse wave signal collected by the second sensor 5, and this can effectively improve accuracy of blood pressure measurement.

In a possible embodiment of this application, in addition to the foregoing structure, some blood pressure measurement devices, for example, a smartwatch or a smart band with a blood pressure measurement function, may each be usually provided with a photoplethysmograph (photoplethysmograph, PPG) module. Still refer to FIG. 2 or FIG. 3. The PPG nodule 14 may be alternatively disposed on the bottom surface of the body 1. In addition, the PPG module 14 may be further disposed in a middle area of the bottom surface of the body 11 (see a circular area in the middle of the bottom surface of the body 1 shown in FIG. 2 or FIG. 3), so as to improve detection accuracy of the PPG module 14.

Still refer to FIG. 2 and FIG. 3. An electrocardiogram (electrocardiogram, ECG) detection module may be further disposed on the smartwatch in this embodiment of this application. The ECG detection module 15 may also be disposed on the bottom surface of the body 1. In addition, the ECG detection module 15 may be further disposed in the middle area of the body 1. For example, the ECG detection module 15 may be disposed around the PPG module 14 (see an arc area in the middle of the bottom surface of the body 1 shown in FIG. 2 or FIG. 3). In this way, an electrocardiogram detection function of the blood pressure measurement device is implemented.

Blood pressure measurement by using a pulse wave velocity is a non-invasive and continuous blood pressure measurement method. As early as 1922, it was found that a pulse wave velocity (pulse wave velocity, PWV) or a pulse wave transit time (pulse wave transit time, PWTT) is related to an arterial blood pressure, and is also related to a vascular space and vascular wall elasticity. The pulse wave velocity is a pressure wave velocity that is generated by ejection during each cardiac pulsation and that is propagated along a big artery wall, is a simple, effective, and economical non-invasive indicator for evaluating arterial vascular stiffness, can comprehensively reflect vascular damage caused by various risk factors, and is an independent predictive factor of cardiovascular evaluation. In addition, the pulse wave velocity can reflect an elastic state of a large and medium arterial system, is non-invasive, simple, effective, and repeatable, and can also reflect a real-time change of an arterial function. On this basis, a person skilled in the art proposes that the following relational expression BP=A·1n (PWV)+B may exist between the blood pressure value BP and the PWV, where A and B are relational expressions obtained through analysis based on a big data fitting function.

It may also be learned from the description of the foregoing embodiment that the blood pressure measurement device may be further provided with the ECG detection module 15 and the PPG module 14. In this way, measurement values of the ECG detection module 15 and the PPG module 14 may be processed to obtain a corresponding PWV and/or PWTT, so that a third blood pressure value BP3 may be obtained by using the PWV and/or the PWTT. In this way, the second blood pressure value BP2 obtained based on the pulse wave signal collected by the second sensor 5 and the third blood pressure value BP3 obtained by using the PWV and/or the PTT based on the photoplethysmographic pulse wave signal collected by the PPG module 14 may be used to calibrate the first blood pressure value BP1 obtained based on the air pressure value, in the airbag 2, collected by the first sensor 4. In this way, the blood pressure value BP of the human body may be obtained based on a mapping relationship among the first blood pressure value BP1, the second blood pressure value BP2, and the third blood pressure value BP3, and BP=C(BP1)+D(BP2)+G(BP3), where C, D, and G are relational expressions obtained through analysis based on a big data fitting function. In this embodiment of this application, the first blood pressure value BP1 is calibrated by using the second blood pressure value BP2 and the third blood pressure value BP3, so that a relatively accurate blood pressure value can be obtained.

It may be understood that, in the foregoing embodiment of this application, blood pressure measurement is implemented on a basis that the airbag 2 is filled with air, so that the airbag 2 can press a blood vessel of the wrist. In addition, when the airbag 2 does not press the blood vessel of the wrist of the human body, the second sensor 5 may be fitted to the wrist, so that the second sensor 5 can collect a pulse wave signal in real time. In this embodiment, a process of calculating a blood pressure value based on the pulse wave signal collected by the second sensor 5 may be: first identifying each feature point of a collected pulse wave, calculating parameters such as a rise slope of a pulse wave, a main wave height, a time length of the pulse wave, and a trough value of the pulse wave by using these feature points, and calculating a characteristic quantity of a pulse wave waveform. Finally, a systolic blood pressure and a diastolic blood pressure may be calculated by substituting the foregoing calculated pulse wave parameters into an established and verified blood pressure regression equation. Therefore, the blood pressure measurement device provided in this application can be used to implement dynamic measurement of a blood pressure when the airbag 2 does not press a blood vessel. In addition, in the dynamic measurement process, the second sensor 5 is only in contact with the skin of the wrist, and does not need to put regular pressure, so that real-time dynamic blood pressure measurement that is not sensitive or even insensitive can be effectively implemented. In this way, impact on a life status of the user can be avoided, and emotion fluctuation of the user in a measurement process can be reduced, so that a blood pressure measurement result is relatively accurate.

In addition, in a possible embodiment of this application, a blood pressure value of a single measurement obtained after the blood pressure value obtained based on the air pressure value data, in the airbag 2, collected by the first sensor 4 is calibrated may be further used as a reference value. Then, a dynamic blood pressure waveform is obtained with reference to a real-time waveform of the pulse wave collected by the second sensor 5. A blood pressure value at any moment of 24 hours in a whole day can be queried based on the dynamic blood pressure waveform, so that masked hypertension and nocturnal hypertension can be effectively identified. This has higher application value in blood pressure measurement. It should be noted that, in this embodiment, the airbag 2 may be detachably connected to the body 1. In this way, after the blood pressure value is obtained based on the air pressure value, in the airbag 2, collected by the first sensor 4, the airbag 2 may be detached from the body 1. This helps improve comfort of wearing the blood pressure measurement device.

According to the blood pressure measurement device provided in this application, when the airbag 2 is filled with air and causes pressure on a blood vessel, a blood pressure value obtained based on the air pressure value data, in the airbag 2, collected by the first sensor 4 may be calibrated, so that accuracy of measuring a blood pressure value of a human body can be effectively improved. In addition, when the airbag 2 does not cause pressure on the blood vessel, the pulse wave signal collected by the second sensor 5 may be used to effectively implement real-time dynamic blood pressure measurement that is not sensitive or even insensitive, and measurement accuracy of this is relatively high.

Figure 12:
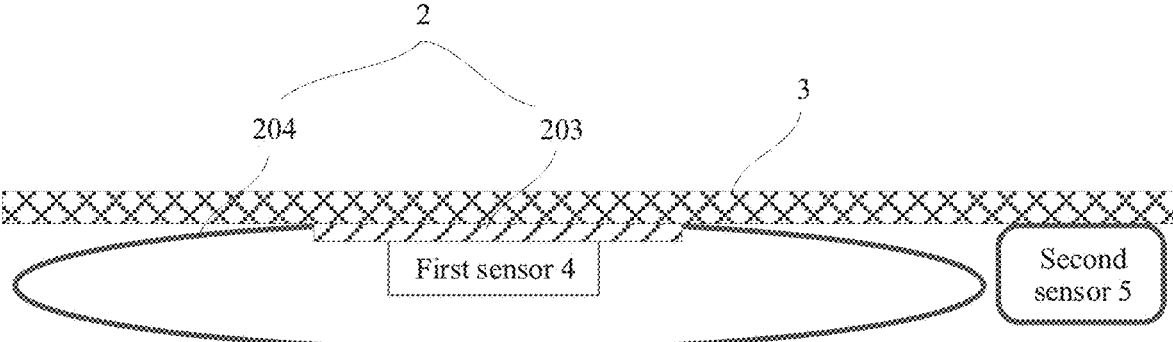
FIG. 12 is a sectional view at A-A of the blood pressure measurement device shown in FIG. 2 according to an embodiment of this application.

It can be learned from the description of the blood pressure measurement device provided in this application in the foregoing embodiment that the first sensor 4 may be configured to measure the air pressure value in the airbag 2. On this basis, it may be understood that the first sensor 4 may be disposed in the cavity 101 of the body 1 and connected to the airbag 2 through an air path. In addition, in some possible embodiments of this application, the first sensor 4 may be directly disposed in the airbag 2. During specific implementation, refer to FIG. 12. FIG. 12 is a sectional view at A-A of the blood pressure measurement device shown in FIG. 2 according to a possible embodiment of this application. In this embodiment, the first sensor 4 may be fastened to an inner side wall of the air cavity of the airbag 2 in a manner such as bonding. For example, the first sensor 4 may be fastened to an inner side wall of a part that is of the airbag 2 and that is in contact with the wrist strap 3, so as to reduce a risk of damage to the first sensor 4 in a process of pressing a blood vessel by the airbag 2.

In addition, in a process of measuring the air pressure value in the airbag 2 by using the first sensor 4, the airbag 2 needs to press the blood vessel, and a contact area between the airbag 2 and the wrist has important impact on a press force of the airbag 2 on the blood vessel. On this basis, in a possible embodiment of this application, to enable the airbag 2 to effectively press a blood vessel, a hard support part 203 may be disposed in the airbag 2, and another part of the airbag 2 other than the hard support part 203 may be disposed as a flexible thin film part 204. Hardness of the hard support part 203 is greater than hardness of the flexible thin film part 204, so that when the airbag 2 is filled with air, a deformation quantity of the hard support part 203 is less than a deformation quantity of the flexible thin film part 204.

Figure 13:
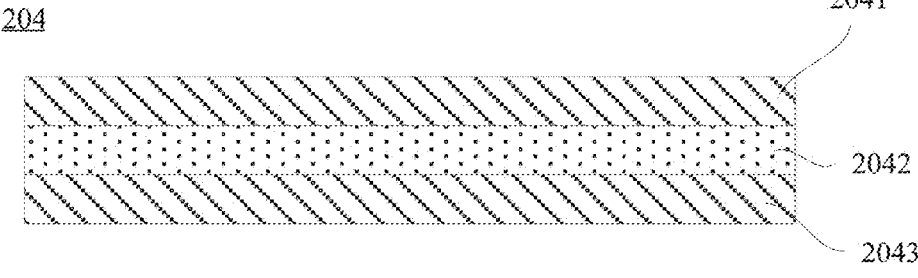
FIG. 13 is a diagram of a structure of a flexible thin film part according to an embodiment of this application.

In this application, a material of the hard support part 203 is not specifically limited, and may be, for example, polyethylene glycol terephthalate (polyethylene glycol terephthalate, PET). In addition, a concave texture may be further disposed on a surface of the hard support part 203, to improve air-filling performance, protect a device, and prevent slip. The flexible thin film part 204 of the airbag 2 may be of a single-layer structure, and a material of the flexible thin film part 204 may be, but is not limited to, a thermoplastic polyurethane (thermoplastic polyurethane, TPU). In addition, to enable the flexible thin film part 204 to have a sufficient tension resistance capability and to further reduce a thickness of the flexible thin film part 204, in a possible embodiment of this application, the flexible thin film part 204 may be disposed as a plurality of layer structures that are stacked. During specific implementation, refer to FIG. 13. FIG. 13 is a diagram of a structure of the flexible thin film part 204 according to a possible embodiment of this application. In this embodiment, the flexible thin film part 204 includes a first-layer structure 2041, a second-layer structure 2042, and a third-layer structure 2043 that are stacked. The second-layer structure 2042 is located between the first-layer structure 2041 and the third-layer structure 2043. Materials of the first-layer structure 2041 and the third-layer structure 2043 may be TPUs. The second-layer structure 2042 may be disposed as a tension-resistant material layer, for example, a fabric layer, and a material of the second-layer structure 2042 may be but is not limited to ice silk. Alternatively, materials of the first-layer structure 2041, the second-layer structure 2042, and the third-layer structure 2043 may be different. For example, the first-layer structure 2041 is a silicone layer, the second-layer structure 2042 is a fabric layer, and the third-layer structure 2043 is a TPU layer.

It may be understood that the description of the manner of disposing the layer structure of the flexible thin film part 204 in the foregoing embodiment is merely some example descriptions provided in this application. In some other possible embodiments of this application, a quantity of layer structures of the flexible thin film part 204 may be increased or decreased based on a specific requirement. For example, to improve wearing comfort, a layer of fabric used to change comfort may be added to a surface of the flexible thin film part 204. In addition, when the flexible thin film part 204 includes a plurality of layer structures that are stacked, adjacent layer structures may be bonded and press-fitted through hot pressing, or bonded by using a double-sided tape, or the like, so as to improve air tightness and structural reliability of the airbag 2.

In a possible embodiment of this application, the hard support part 203 may be an independent structure, and may be disposed inside the airbag 2. In addition, the hard support part 203 may be fastened to an inner side wall of the airbag 2 in a manner including but not limited to bonding. For example, in the embodiment shown in FIG. 12, the hard support part 203 may be fastened to an inner side wall of a part that is of the airbag 2 and that is in contact with the wrist strap 3. In another possible embodiment of this application, the hard support part 203 may be a part of the airbag 2, and the hard support part 203 and the flexible thin film part 204 may be connected to form an air cavity of the airbag 2, to simplify a structure of the airbag 2. In this application, the hard support part 203 is disposed, so that when the blood pressure measurement device is worn on the wrist, the hard support part 203 can press the airbag 2 toward the wrist. In addition, it may be understood that, an effective contact area between the airbag 2 and the wrist may be adjusted by adjusting the width of the hard support part 203, so as to meet a press requirement of the airbag 2 on the wrist, and this helps improve accuracy of blood pressure measurement.

It should be noted that, because hardness of the hard support part 203 is greater than hardness of the flexible thin film part 204, in the embodiment shown in FIG. 12 of this application, the first sensor 4 may be fastened to the hard support part 203 in a manner such as bonding, to improve structural reliability of the first sensor 4. In addition, when the first sensor 4 is disposed in the airbag 2, the first sensor 4 may be an absolute pressure air pressure sensor. In this embodiment, the air cavity of the airbag 2 may be a sealed cavity 101.

Figure 14:
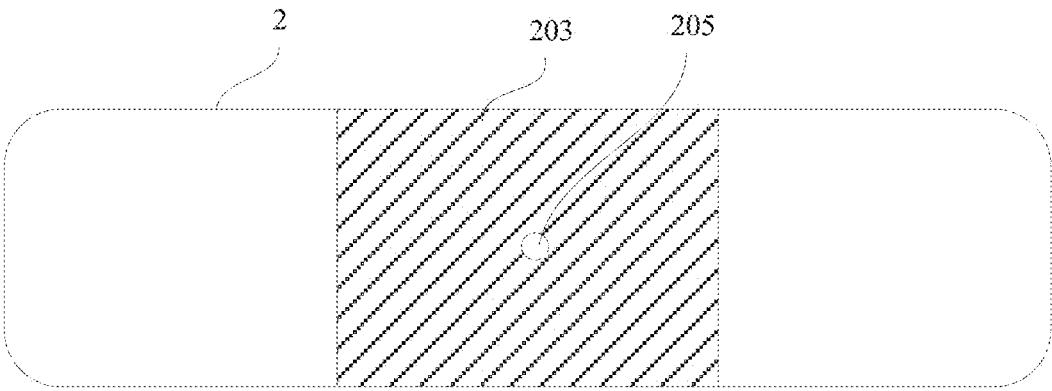
FIG. 14 is a top view of an airbag according to an embodiment of this application.

In another possible embodiment of this application, the first sensor 4 may be alternatively a differential pressure air pressure sensor. When the differential pressure air pressure sensor works, the differential pressure air pressure sensor needs to be placed in two environments with different air pressure values. Therefore, in this embodiment, the airbag 2 may be provided with an air hole 205. In this way, one side of the first sensor 4 may be connected to an outside atmosphere by using the air hole 205, and the other side may communicate with the air cavity of the airbag 2. In addition, it may be learned from the description of the foregoing embodiment that the first sensor 4 may be disposed on the hard support part 203. Refer to FIG. 14, FIG. 14 is a top view of the airbag 2 according to a possible embodiment of this application. In this embodiment, the air hole 205 may be provided on the hard support part 203. To enable the air hole 205 to communicate with the outside atmosphere, the air hole 205 may be disposed opposite to a buckle hole of the wrist strap 3, so that the wrist strap 3 may be prevented from covering the air hole 205. In addition, the air hole 205 is disposed opposite to the buckle hole, so as to avoid opening an additional hole on the wrist strap 3, so as to simplify a processing process of the wrist strap 3, and avoid affecting appearance and beauty of the wrist strap 3.

It should be noted that, in this application, in addition to the manner, described in the foregoing embodiment, in which the second sensor 5 is arranged side by side with the airbag 2 on the wrist strap 3 or exposed from the recess area of the airbag 2, in some possible embodiments of this application, the second sensor 5 and the airbag 2 may be arranged in a stacked manner. For example, the second sensor 5 may be arranged between the airbag 2 and the wrist strap 3. In this embodiment, the second sensor 5 may be but is not limited to a PPG module. In this way, after the first sensor 4 measures the air pressure value in the airbag 2 to obtain the first blood pressure value, the airbag 2 may be detached from the body 1, so as to obtain the second blood pressure value based on the first blood pressure value and the pulse wave signal measured by the second sensor 5. In addition, because the second sensor 5 may collect a real-time dynamic pulse wave, a real-time dynamic blood pressure waveform may be obtained by using the blood pressure measurement device in this embodiment. Therefore, a blood pressure value at any moment of 24 hours in a whole day can be queried based on the dynamic blood pressure waveform, so that masked hypertension and nocturnal hypertension can be effectively identified. This has higher application value in blood pressure measurement.

In some other possible embodiments of this application, the second sensor 5 may be alternatively disposed in the airbag 2. In this embodiment, the second sensor 5 may be a flexible pressure pulse wave sensor, and may be fitted to a wrist of a human body when no pressure is put on the airbag 2, to dynamically measure a pulse wave. It may be understood that, in this embodiment, the second sensor may be disposed on an inner wall of a part that is of the airbag 2 and that is fitted to the wrist of the human body, so as to implement fitting between the second sensor 5 and the wrist, thereby improving accuracy of pulse wave measurement by the second sensor.

In this application, a quantity of second sensors 5 is not limited. In a possible embodiment, there may be a plurality of second sensors 5, and the plurality of second sensors 5 may form an array, so that multi-point measurement of a pulse wave can be implemented, and this can meet use requirements of users with different wrist circumferences. After the plurality of second sensors 5 separately collect pulse wave signals, the pulse wave signals are selected based on a specific situation, or the pulse wave signals are combined for subsequent blood pressure value calculation, thereby helping improve accuracy of blood pressure measurement.

When the airbag 2 presses the wrist, it is only required that effective extrusion on a specific pulse can be implemented to obtain an effective pulse signal. However, if the width of the airbag 2 is relatively large, the user may feel uncomfortable, for example, feel stuffy. This affects a user emotion, causes a relatively large error in the obtained pulse signal, and affects accuracy of blood pressure measurement. To resolve this problem, in this application, a narrowing design solution of the airbag 2 is proposed, to improve comfort of a user when wearing the blood pressure measurement device.

Figure 15A:
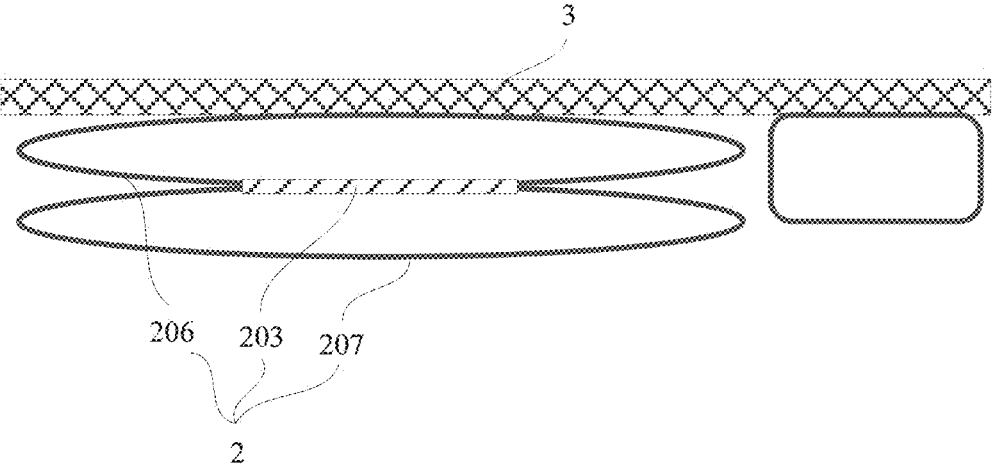
FIG. 15a is a sectional view at A-A of the blood pressure measurement device shown in FIG. 2 according to another embodiment of this application.

During specific implementation, refer to FIG. 15*a*. FIG. 15*a* is a sectional view at A-A of the blood pressure measurement device shown in FIG. 2 according to another possible embodiment of this application. In this embodiment, the airbag 2 may include at least two air chambers. In a direction from the wrist strap 3 to the wrist, the at least two air chambers are arranged in a stacked manner. In addition, the at least two air chambers may not communicate. For example, in the embodiment shown in FIG. 15*a*, the airbag 2 includes two air chambers that may be respectively denoted as a first air chamber 206 and a second air chamber 207. The first air chamber 206 is located between the wrist strap 3 and the second air chamber 207, the first air chamber 206 is separately connected to the wrist strap 3 and the second air chamber 207, and the first air chamber 206 does not communicate with the second air chamber 207. When the two air chambers are connected to the body 1, each air chamber may be connected to the body 1 through one air nozzle 202. For a connection manner, refer to the description of the connection between the airbag 2 and the body 1 through the air nozzle 202 in the foregoing embodiment. Details are not described herein again. In this embodiment of this application, the airbag 2 is disposed as at least two air chambers that are stacked. In a case of a same air filling volume, compared with an airbag 2 having only one air chamber, the air filling volume of the airbag 2 may be ensured by reducing a width of each air chamber, thereby facilitating implementation of a narrowing design of the entire airbag 2.

Still refer to FIG. 15*a*. In this embodiment, the hard support part 203 may be disposed at, but is not limited to, a connection portion between the first air chamber 206 and the second air chamber 207. In this way, in a process of filling the first air chamber 206 and the second air chamber 207 with air, the hard support part 203 may press the second air chamber 207 toward the wrist of the human body, so that there is a press-fitting area that meets a measurement requirement between the airbag 2 and the wrist.

Figure 15B:
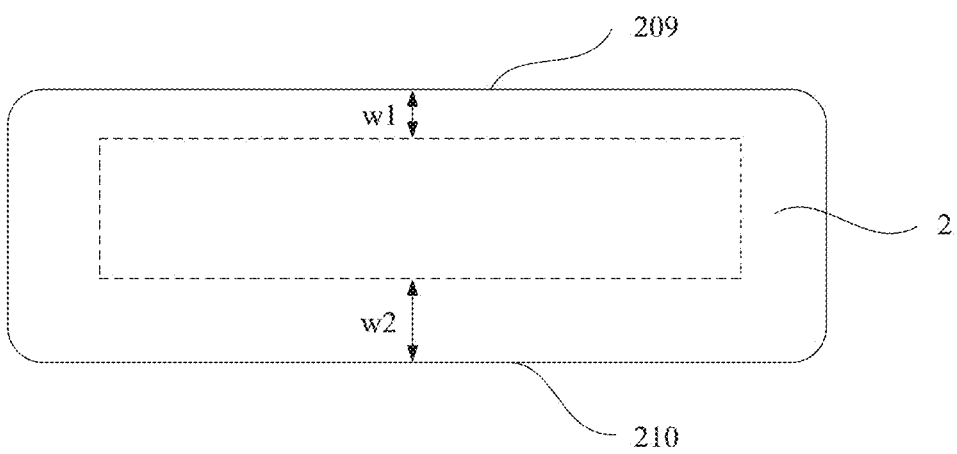
FIG. 15b is a top view of an airbag according to an embodiment of this application.

It should be noted that, in this application, a connection portion between two air chambers is an area in which two adjacent air chambers are connected. For example, refer to FIG. 15*b*. FIG. 15*b* is a top view of the airbag. An area enclosed by a dashed-line box in FIG. 15*b* represents a connection portion between the two air chambers, and the two air chambers may be connected only at each box edge of the dashed-line box, or may be connected in an entire area enclosed by the dashed-line box. This is not limited in this application.

Because wrist forms of different users are different, for example, wrists of some users are gradually widened in a direction from a palm to an elbow. To enable the airbag 2 to adapt to use requirements of users having different wrist forms, still refer to FIG. 15*b*. In a width direction of the airbag 2, the airbag 2 may include a first edge 209 and a second edge 210. When the blood pressure measurement device is worn on the wrist of the user, the first edge 209 is disposed closer to the palm than the second edge 210. In addition, a minimum distance w1 between the first edge 209 and the connection portion is less than a minimum distance w2 between the second edge 210 and the connection portion, so that a requirement for fitting the airbag 2 to the wrist can be met.

Figure 16:
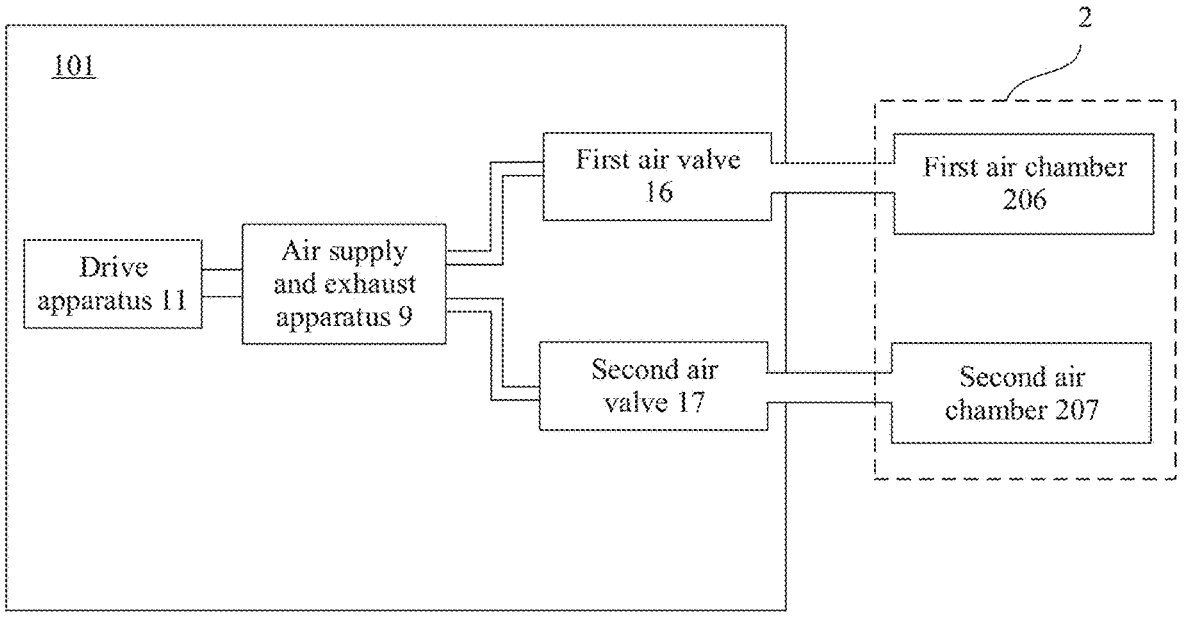
FIG. 16 is a block diagram of a structure of a blood pressure measurement device according to another embodiment of this application.

FIG. 16 is a block diagram of a structure of the blood pressure measurement device according to another possible embodiment of this application. In the embodiment shown in FIG. 16, the airbag 2 may use the structure of the embodiment shown in FIG. 15*a*. The first air chamber 206 may be connected to the air supply and exhaust apparatus 9 through a first air valve 16, and the second air chamber 207 may be connected to the air supply and exhaust apparatus 9 through a second air valve 17, so that the air supply and exhaust apparatus 9 can perform air filling or exhausting for the first air chamber 206 and the second air chamber 207. In addition, in this embodiment, structures such as the processor 12, the drive circuit 13, the air path cavity 6, the first sensor 4, and the second sensor 5 are omitted. For details, refer to the blood pressure measurement device shown in FIG. 9. For example, the air supply and exhaust apparatus 9 may be connected to the first air valve 16 and the second air valve 17 through the air path cavity 6.

Figure 17:
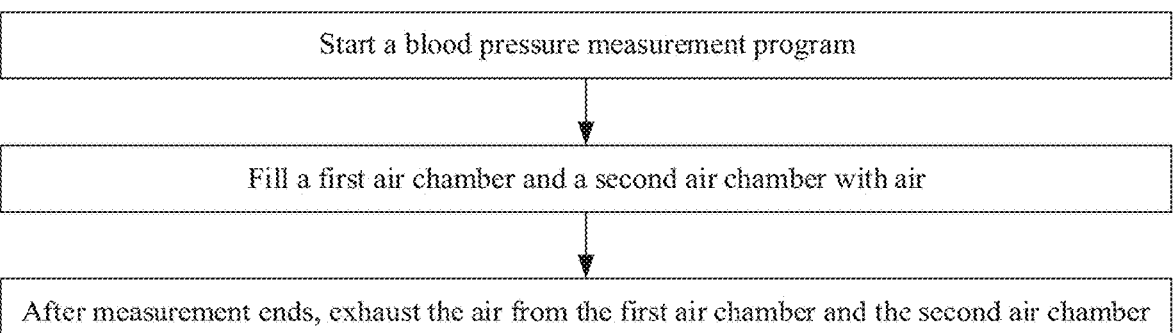
FIG. 17 is a flowchart of steps of blood pressure measurement according to an embodiment of this application.

Based on the blood pressure measurement device shown in FIG. 16, the following describes steps of applying the blood pressure measurement device to perform blood pressure measurement. FIG. 17 is a flowchart of steps of blood pressure measurement according to a possible embodiment.

Step 1: Start a blood pressure measurement program. The measurement program may be started by triggering, by a user, a start button on the blood pressure measurement device. In addition, the blood pressure measurement device may be further connected to an external terminal device (for example, a mobile phone or a notebook computer) in a wireless or wired manner, so that a blood pressure measurement program may be started by using the external terminal device.

Step 2: Fill the first air chamber 206 and the second air chamber 207 with air. In this step, first, the first air valve 16 may be opened and the second air valve 17 may be closed, so as to fill the first air chamber 206 with a specific amount of air by using the air supply and exhaust apparatus 9. Then, the first air valve 16 is closed and the second air valve 17 is opened, so that the second air chamber 207 is filled with a specific amount of air by using the air supply and exhaust apparatus 9, so that the air filled in the first air chamber 206 and the second air chamber 207 can reach a pressure required for measurement.

It should be noted that, before the first air chamber 206 and the second air chamber 207 are filled with air, operations such as frequency sweep and pressure adjustment may be performed on the air supply and exhaust apparatus 9 first, so as to adjust a working state of the air supply and exhaust apparatus 9. In addition, in step 2, a sequence of filling the first air chamber 206 and the second air chamber 207 with air is not limited. In a possible embodiment, the second air chamber 207 may be first filled with air, and then the first air chamber 206 is filled with air.

Step 3: After the measurement ends, exhaust the air from the first air chamber 206 and the second air chamber 207 by using the air supply and exhaust apparatus 9. In this step, an air exhausting sequence of the first air chamber 206 and the second air chamber 207 is not limited. For example, the first air valve 16 may be first opened to make the second air valve 17 in a closed state, so as to exhaust the first air chamber 206, and then the second air valve 17 is opened to exhaust the second air chamber 207. For another example, the first air valve 16 and the second air valve 17 may be opened at the same time, so as to exhaust the air from the two air chambers at the same time.

It may be understood that, in the foregoing air filling and exhausting process, the first sensor 4 may collect air pressure value data in the first air chamber 206 and/or the second air chamber 207 of the airbag 2, and the second sensor 5 collects a pulse wave signal of the user, so as to obtain a blood pressure value of the user under test with reference to data collected by the first sensor 4 and the second sensor 5.

In some possible embodiments of this application, the first air chamber 206 and the second air chamber 207 of the airbag 2 may further communicate. In this way, in a process in which the blood pressure measurement device is used to perform blood pressure measurement, the first air chamber 206 and the second air chamber 207 may be filled with air at the same time, and after the measurement is completed, the air is exhausted from the first air chamber 206 and the second air chamber 207 at the same time, so as to effectively simplify a measurement process of the blood pressure measurement device. In addition, in this way, the airbag 2 may be further connected to the body through one air nozzle.

Figures 18, 19:
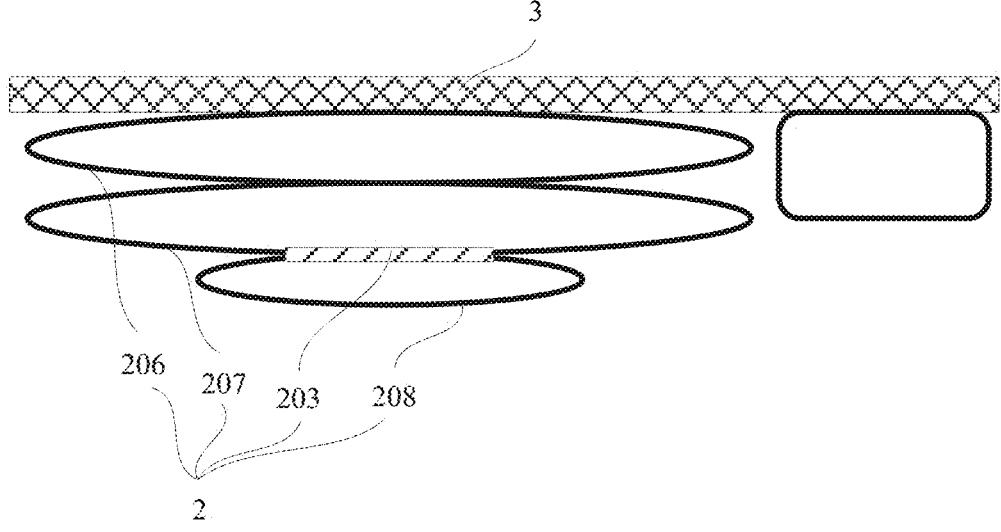
FIG. 18 is a sectional view at A-A of the blood pressure measurement device shown in FIG. 2 according to another embodiment of this application.
FIG. 19 is a block diagram of a structure of a blood pressure measurement device according to another embodiment of this application.

In addition, refer to FIG. 18. FIG. 18 is a sectional view at A-A of the blood pressure measurement device shown in FIG. 2 according to another possible embodiment of this application. In this embodiment, the airbag 2 may include three air chambers: a first air chamber 206, a second air chamber 207, and a third air chamber 208. The first air chamber 206 is connected to the wrist strap 3, the second air chamber 207 is located between the first air chamber 206 and the third air chamber 208, and the second air chamber 207 is separately connected to the first air chamber 206 and the third air chamber 208. In this case, the third air chamber

208 may be configured to be in contact with the wrist. In this embodiment, an air volume of the third air chamber 208 may also be less than an air volume of the first air chamber 206 and is less than in air volume of the second air chamber 207. During specific implementation, under a condition that other sizes of the three air chambers are the same, a width of the third air chamber 208 may be less than a width of the first air chamber 206, and the width of the third air chamber 208 may be less than a width of the second air chamber 207. The widths of the first air chamber 206 and the second air chamber 207 may be the same or may be different. Because the third air chamber 208 may be in contact with the wrist, and because the air volume of the third air chamber 208 is less than those of the other two air chambers, the third air chamber 208 may be filled with less air. In this way, an effective contact area between the third air chamber 208 and the wrist may be relatively large, so that there is a press force that meets a measurement requirement between the airbag 2 and the wrist, and this helps improve measurement accuracy of the blood pressure measurement device.

Still refer to FIG. 18. In this embodiment of this application, the hard support part 203 may be disposed at a connection portion between the second air chamber 207 and the third air chamber 208. In this way, in a process of filling the first air chamber 206 and the second air chamber 207 with air, the hard support part 203 may press the third air chamber 208 toward the wrist of the human body, so that there is a press-fitting area that meets a measurement requirement between the third air chamber 208 and the wrist.

It should be noted that, in some other possible embodiments of this application, the hard support part 203 may be alternatively disposed between the first air chamber 206 and the second air chamber 207, to further increase a press-fitting area between the airbag 2 and the wrist. In addition, the first air chamber 206 and the second air chamber 207 may communicate by drilling a hole at a connection portion between the first air chamber 206 and the second air chamber 207, and the second air chamber 207 does not communicate with the third air chamber 208. In this way, the first air chamber 206 and the second air chamber 207 may communicate with the air supply and exhaust apparatus through the first air valve, and the third air chamber 208 may communicate with the air supply and exhaust apparatus through the second air valve. Because a structure of the blood pressure measurement device provided in this embodiment may be disposed with reference to FIG. 16, and for a blood pressure measurement process of the blood pressure measurement device, reference may be made with reference to FIG. 17, details are not described herein again. In addition, in some possible embodiments of this application, the first air chamber 206, the second air chamber 207, and the third air chamber 208 may further communicate with one another, so that the airbag 2 may be connected to the body by using one air nozzle, thereby improving structural reliability of the blood pressure device.

It can be learned from the description of the foregoing embodiment that, in the blood pressure measurement device provided in this application, in addition to components (for example, the airbag 2 and the body 1) that are connected through an air path, some components may be connected through an electrical connection cable. For example, the second sensor 5 needs to be electrically connected to a component such as the processor 12 in the cavity 101 of the body 1 through an electrical connection cable. For example, when the second sensor 5 is disposed on the wrist strap 3, the second sensor 5 may be electrically connected to a component such as the processor 12 through an electrical connection cable that passes through the wrist strap 3.

In addition, based on the description of the foregoing embodiment, in some embodiments of this application, the first sensor 4 may be disposed in the airbag 2. In this case, the first sensor 4 also needs to be electrically connected to a component such as the processor 12 in the body 1 through an electrical connection cable. FIG. 19 shows a manner in which the first sensor 4 is electrically connected to a component such as the processor 12 in the body 1 according to a possible embodiment of this application. In this embodiment, the airbag 2 may be provided with an electrical connection portion, and the electrical connection portion may be provided in a part that is of the airbag 2 and that is used to connect to the body 1, for example, the air nozzle 202 or the connection hole 102 on the airbag 2. An example in which an electrical connection portion is disposed on the air nozzle 202 of the airbag 2 is used herein to describe implementation of an electrical connection manner between the first sensor 4 and a component such as the processor 12 in the body 1. In this case, the body 1 may be provided with the connection hole 102.

Still referring to FIG. 19, the electrical connection portion may be disposed on a surface of the air nozzle 202, so as to avoid impact on air path connection between the air nozzle 202 and the body 1. In addition, the electrical connection portion may include a signal layer 19. The signal layer 19 may be used as a connection medium for implementing electrical connection between the first sensor 4 and a component such as the processor 12 in the cavity of the body 1. During specific implementation, the first sensor 4 may be electrically connected to the signal layer 19 through a first electrical connection cable 18, and then the signal layer 19 is electrically connected to a component such as the processor 12 in the cavity of the body 1 through a second electrical connection cable (not shown in FIG. 19).

It should be noted that, in this application, the first electrical connection cable 18 may be connected to the signal layer 19 in a manner including but not limited to welding. In addition, the signal layer 19 may also be connected to the second electrical connection cable in a welding manner, or the second electrical connection cable may include a spring part, where the spring part is disposed at the connection hole 102. Therefore, when the air nozzle 202 is inserted into the connection hole 102, the signal layer 19 can be in conductive contact with the spring part.

Because the first electrical connection cable 18 may include a plurality of transmission lines used to implement different functions, in this application, the signal layer 19 may include a plurality of sub-signal layers, so that each sub-signal layer is correspondingly connected to one transmission line. For example, the signal layer 19 may include a first sub-signal layer 1901 and a second sub-signal layer 1902. The first sub-signal layer 1901 may be electrically connected to the first sensor 4 through one transmission line, and the second sub-signal layer 1902 may be electrically connected to the first sensor 4 through another transmission line. For example, the first sub-signal layer 1901 may be electrically connected to the first sensor 4 through a signal transmission line in the first electrical connection cable 18, and the second sub-signal layer 1902 may be electrically connected to the first sensor 4 through a ground transmission line in the first electrical connection cable 18. It may be understood that when the signal layer 19 is electrically connected to a component such as the processor 12 in the cavity of the body 1 through the second electrical connection cable, the first sub-signal layer 1901 is electrically connected to a same transmission line in the first electrical connection cable 18 and the second electrical connection cable, and the second sub-signal layer 1902 is electrically connected to a same transmission line in the first electrical connection cable 18 and the second electrical connection cable, so that the first sensor 4 is effectively electrically connected to a component such as the processor 12 in the cavity of the body 1.

Figures 20A, 20B:
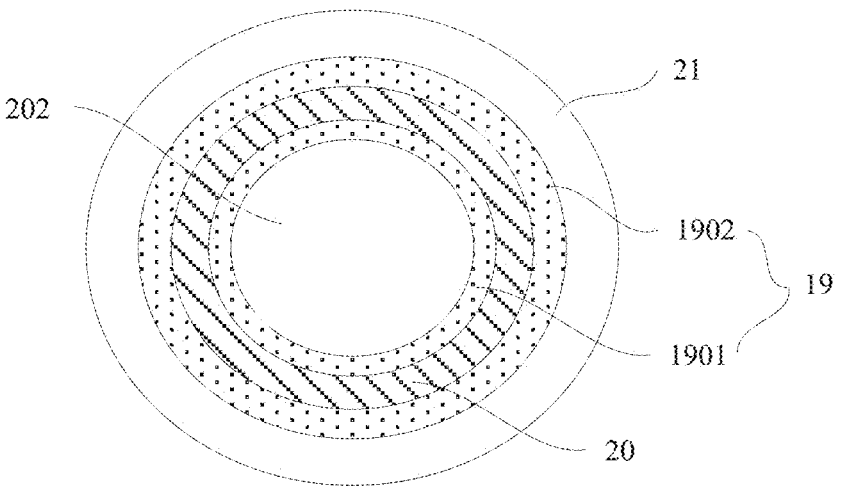
FIG. 20a to FIG. 20c are diagrams of structures of cross sections of an air nozzle according to this application.

When the first sub-signal layer 1901 and the second sub-signal layer 1902 are specifically disposed, refer to FIG. 20a. FIG. 20a is a diagram of a structure of a cross section of the air nozzle 202 according to a possible embodiment of this application. In this embodiment, a cross section of the air nozzle 202 in a radial direction is shown. Cross-sectional shapes of both the first sub-signal layer 1901 and the second sub-signal layer 1902 may be annular shapes, and the second sub-signal layer 1902 may be sleeved around the first sub-signal layer 1901. In addition, to avoid a short circuit between the two sub-signal layers, an insulation layer 20 may be disposed between the two sub-signal layers.

Figure 20C:
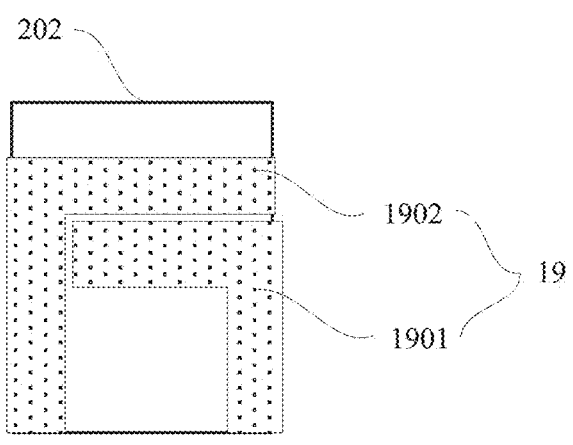

The first sub-signal layer 1901 and the second sub-signal layer 1902 may be disposed in any other possible manner in addition to the foregoing disposing manner shown in FIG. 20a. For example, refer to FIG. 20b. FIG. 20b is a diagram of a structure of a cross section of the air nozzle 202 in a radial direction according to another possible embodiment of this application. In this embodiment, cross-sectional shapes of both the first sub-signal layer 1901 and the second sub-signal layer 1902 may be parts of annular shapes, radiuses of the cross-sectional shapes of the two sub-signal layers may be the same or may be different, and the insulation layer 20 is disposed between the two sub-signal layers, so that the two sub-signal layers are not connected to each other, and the first sub-signal layer 1901 and the second sub-signal layer 1902 are not connected to each other. FIG. 20c is still a diagram of a structure of a cross section of the air nozzle 202 in a circumferential direction according to a possible embodiment of this application. In this embodiment, both the first sub-signal layer 1901 and the second sub-signal layer 1902 are disposed on a surface of the air nozzle 202, and the first sub-signal layer 1901 and the second sub-signal layer 1902 are arranged in a staggered manner in the axial direction of the air nozzle 202, The first sub-signal layer 1901 includes an annular portion disposed around the circumferential direction of the air nozzle 202, and a first extension portion disposed in the axial direction of the air nozzle 202. The second sub-signal layer 1902 includes a semi-annular portion disposed around the circumferential direction of the air nozzle 202, and a second extending portion disposed in the axial direction of the air nozzle 202. In addition, in the axial direction of the air nozzle 202, the annular portion of the first sub-signal layer 1901 and the semi-annular portion of the second sub-signal layer 1902 are arranged in a staggered manner.

It may be understood that, in the foregoing embodiment, a manner of disposing the signal layer 19 is described only by using an example in which the signal layer 19 includes two sub-signal layers. When the signal layer 19 includes more than two sub-signal layers, the signal layer 19 may be disposed with reference to the foregoing signal layer including two sub-signal layers, and details are not described herein again.

In this application, to prevent the signal layer 19 from being exposed, a protective layer 21 may be disposed on a surface of the signal layer 19. The protective layer 21 may be an insulation material layer coated on the surface of the signal layer 19, and a material of the protective layer 21 may be but is not limited to plastic, silicone, rubber, or the like, to reduce a risk of oxidation, a short circuit, or the like of the signal layer 19.

Figure 21A:
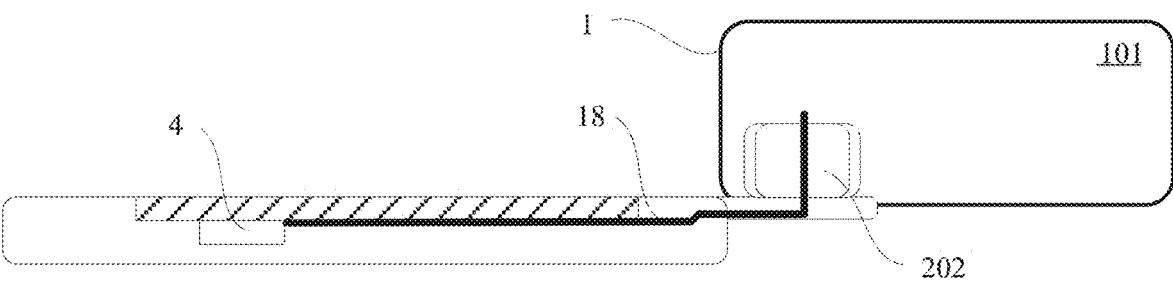
FIG. 21a and FIG. 21b are block diagrams of structures of a blood pressure measurement device according to another embodiment of this application.

In addition to the foregoing manner in which the first sensor 4 is electrically connected to a component such as the processor 12 in the cavity of the body 1 through the airbag 2, the first sensor 4 may be directly electrically connected to a component such as the processor 12 in the cavity 101 of the body 1 through the first electrical connection cable 18. During specific implementation, refer to FIG. 21a. FIG. 21a shows a manner in which the first sensor 4 is electrically connected to a component such as the processor 12 in the cavity 101 of the body 1 according to another possible embodiment of this application. In this embodiment, the first electrical connection cable 18 that is connected to and that comes from the first sensor 4 may extend into the cavity 101 of the body 1 after passing through a part (for example, the air nozzle 202 or the connection hole 102 on the airbag 2) that is of the airbag 2 and that is used to connect to the body 1, and is electrically connected to a component such as the processor 12 in the cavity 101 of the body 1. During specific implementation, the first electrical connection cable 18 may pass through the airbag 2 and enter the air path cavity mentioned in the foregoing embodiment, and then a module that enables the first electrical connection cable 18 to be electrically connected to the component in the cavity 101 of the body 1 is designed in the air path cavity, so that the first electrical connection cable 18 is electrically connected to the component in the cavity 101 of the body 1 by using the module in the air path cavity. In this way, a structure of the airbag 2 can be effectively simplified, and an electrical connection manner between the first sensor 4 and a component such as the processor 12 in the cavity 101 of the body 1 is simplified.

Figure 21B:
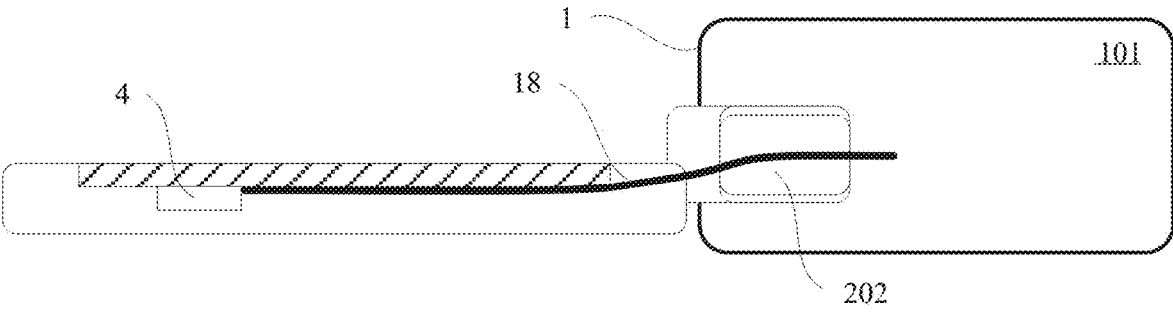

It may be understood that, in this application, when connection portions of the airbag 2 and the body 1 are different, a manner in which the first electrical connection cable 18 used to connect the first sensor 4 and the component in the cavity 101 of the body 1 passes through the body 1 is slightly different. For example, in the embodiment shown in FIG. 21a, the airbag 2 may be connected to the bottom surface of the body 1. In this case, the first electrical connection cable 18 used to connect the first sensor 4 and the component in the body 1 may pass through the bottom surface of the body 1 and enter the cavity 101 of the body 1. For another example, in the embodiment shown in FIG. 21b, the airbag 2 may be connected to a side face of the body 1. In this case, the first electrical connection cable 18 used to connect the first sensor 4 and the component in the cavity 101 of the body 1 may pass through the side face of the body 1 and enter the cavity 101 of the body 1. In addition, in the embodiments shown in FIG. 21a and FIG. 21b, electrical connection between the first sensor 4 and a component in the cavity 101 of the body 1 is described by using an example in which the airbag 2 includes one air chamber. When the airbag 2 includes a plurality of air chambers, an electrical connection manner between the first sensor 4 located in the airbag 2 and the component in the cavity 101 of the body 1 may be set with reference to the embodiments shown in FIG. 21a and FIG. 21b. Details are not described herein again.

It should be noted that, in some possible embodiments of this application, when the second sensor 5 is electrically connected to the component in the cavity 101 of the body, the connection may be set with reference to the description of the electrical connection manner between the first sensor 4 and the component in the cavity 101 of the body in the foregoing embodiment. The first sensor 4 and the second sensor 5 may be electrically connected to components in the cavity 101 of the body through different electrical connection cables.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A blood pressure measurement device, comprising a body, a wrist strap, an airbag, an air supply and exhaust apparatus, a first sensor, and a second sensor, wherein:
   the body comprises a cavity, and the air supply and exhaust apparatus is disposed in the cavity;
   the airbag comprises an air cavity, and the airbag is connected to an end of the body;
   the air supply and exhaust apparatus comprises an air intake path and an air exhaust path, and the air supply and exhaust apparatus communicates with the air cavity of the airbag through a first air path;
   the first sensor communicates with the air cavity of the airbag to measure an air pressure value in the air cavity;
   the second sensor is configured to measure a pulse wave signal;
   the wrist strap is connected to the end of the body, and the second sensor is arranged on the wrist strap and is located on a same side of the wrist strap as the airbag;
   a blood pressure value is obtained based on the air pressure value measured by the first sensor and the pulse wave signal measured by the second sensor; and
   the airbag comprises a hard support part and a flexible thin film part, and hardness of the hard support part is greater than hardness of the flexible thin film part.

2. The blood pressure measurement device according to claim 1, wherein the airbag and the second sensor are arranged side by side in a width direction of the wrist strap.

3. The blood pressure measurement device according to claim 1, wherein the airbag comprises a recess area, and the second sensor is located in the recess area.

4. The blood pressure measurement device according to claim 1, wherein the airbag comprises at least two air chambers, the at least two air chambers are arranged in a stacked manner, and the at least two air chambers communicate, and wherein the hard support part is disposed at a connection portion between two adjacent air chambers.

5. The blood pressure measurement device according to claim 3, wherein the airbag comprises a first air chamber, a second air chamber, and a third air chamber, the second air chamber is located between the first air chamber and the third air chamber, the first air chamber is connected to the wrist strap, the second air chamber is separately connected to the first air chamber and the third air chamber, and the first air chamber, the second air chamber, and the third air chamber communicate, and wherein the hard support part is disposed at a connection portion between the second air chamber and the third air chamber.

6. The blood pressure measurement device according to claim 5, wherein an air volume of the third air chamber is less than an air volume of the first air chamber, and the air volume of the third air chamber is less than an air volume of the second air chamber.

7. The blood pressure measurement device according to according to claim 3, wherein in a width direction of the airbag, the airbag comprises a first edge and a second edge, and when the blood pressure measurement device is worn on a wrist, the first edge is disposed closer to a palm than the second edge, and wherein a minimum distance between the first edge and a connection portion is less than a minimum distance between the second edge and the connection portion.

8. The blood pressure measurement device according to claim 1, wherein:

the body comprises a connection hole, the airbag is provided with an air nozzle, and the air nozzle is directly inserted into the connection hole; or the air nozzle is inserted into the connection hole after passing through the wrist strap.

9. The blood pressure measurement device according to claim 1, wherein the first sensor is arranged in the cavity of the body, and the first sensor communicates with the air cavity of the airbag through a second air path.

10. The blood pressure measurement device according to claim 1, wherein the first sensor is arranged in the air cavity of the airbag.

11. The blood pressure measurement device according to claim 9, wherein the first sensor is electrically connected to a component in the cavity of the body through a first electrical connection cable.

12. The blood pressure measurement device according to claim 8, wherein the airbag comprises the air nozzle, the airbag is connected to the body through the air nozzle, a signal layer is disposed on a surface of the air nozzle, a first electrical connection cable is electrically connected to the signal layer, and the signal layer is electrically connected to a component in the cavity of the body through a second electrical connection cable.

13. The blood pressure measurement device according to claim 12, wherein the signal layer comprises a first sub-signal layer and a second sub-signal layer, the first sub-signal layer and the second sub-signal layer are separately and electrically connected to the first sensor through the first electrical connection cable, and the first sub-signal layer and the second sub-signal layer are separately and electrically connected to a component in the cavity through the second electrical connection cable.

14. The blood pressure measurement device according to claim 13, wherein in a radial direction of the air nozzle, cross-sectional shapes of both the first sub-signal layer and the second sub-signal layer are annular shapes, and the second sub-signal layer is sleeved around the first sub-signal layer.

15. The blood pressure measurement device according to claim 13, wherein in a radial direction of the air nozzle, cross-sectional shapes of both the first sub-signal layer and the second sub-signal layer are parts of annular shapes, and the first sub-signal layer and the second sub-signal layer are not connected to each other.

16. The blood pressure measurement device according to claim 13, wherein the first sub-signal layer comprises an annular portion disposed around an axial direction of the air nozzle and a first extension portion disposed in the axial direction of the air nozzle, and the second sub-signal layer comprises a semi-annular portion disposed around the axial direction of the air nozzle and a second extension portion disposed in the axial direction of the air nozzle, and wherein the annular portion and the semi-annular portion are arranged in a staggered manner in the axial direction of the air nozzle.

17. The blood pressure measurement device according to claim 8, wherein the airbag comprises the air nozzle, the airbag is connected to the body through the air nozzle, and a first electrical connection cable extends into the cavity of the body through the air nozzle and is electrically connected to a component in the cavity.

18. The blood pressure measurement device according to claim 1, wherein:

the blood pressure measurement device further comprises a photoplethysmograph (PPG) module, and the PPG module is disposed on a bottom surface of the body; and the blood pressure value is obtained based on a PPG pulse wave signal measured by the PPG module.

19. The blood pressure measurement device according to claim 1, wherein the airbag is detachably connected to the body.

20. A blood pressure measurement device, comprising a body, an airbag, an air supply and exhaust apparatus, a first sensor, and a second sensor, wherein:

the body comprises a cavity, and the air supply and exhaust apparatus is disposed in the cavity;

the airbag comprises an air cavity, and the airbag is detachably connected to an end of the body;

the air supply and exhaust apparatus comprises an air intake path and an air exhaust path, and the air supply and exhaust apparatus communicates with the air cavity of the airbag through a first air path;

the first sensor communicates with the air cavity of the airbag to measure an air pressure value in the air cavity, and a first blood pressure value is obtained based on the air pressure value measured by the first sensor;

when the air cavity of the airbag is not filled with air, the second sensor obtains a pulse wave signal, and obtains a second blood pressure value based on the first blood pressure value and the pulse wave signal;

the airbag and the second sensor are arranged in a stacked manner; and the blood pressure measurement device further comprises a wrist strap, the wrist strap is connected to the end of the body, the second sensor is arranged on the wrist strap, and the second sensor is located between the airbag and the wrist strap.

* * * * *